(12) United States Patent
Kato et al.

(10) Patent No.: US 9,074,176 B2
(45) Date of Patent: Jul. 7, 2015

(54) CULTURE MEDIUM ADDITIVE FOR USE IN SERUM-FREE CULTURING OF ANIMAL CELL, KIT AND USE THEREOF

(75) Inventors: Yukio Kato, Hiroshima (JP); Jin Chang Shao, Higashihiroshima (JP); Yuki Katsura, Higashihiroshima (JP); Koichiro Tsuji, Hiroshima (JP)

(73) Assignee: Two Cells Co., Ltd., Hiroshima (JP)

(*) Notice: Subject to any disclaimer, the term of this patent is extended or adjusted under 35 U.S.C. 154(b) by 752 days.

(21) Appl. No.: 12/160,481

(22) PCT Filed: Jan. 11, 2007

(86) PCT No.: PCT/JP2007/050232
§ 371 (c)(1),
(2), (4) Date: Jul. 10, 2008

(87) PCT Pub. No.: WO2007/080919
PCT Pub. Date: Jul. 19, 2007

(65) Prior Publication Data
US 2010/0279412 A1 Nov. 4, 2010

(30) Foreign Application Priority Data
Jan. 13, 2006 (JP) .................. 2006-006706

(51) Int. Cl.
*C12N 5/02* (2006.01)
*C12N 5/00* (2006.01)
(52) U.S. Cl.
CPC .......... *C12N 5/0031* (2013.01); *C12N 2500/14* (2013.01); *C12N 2500/16* (2013.01); *C12N 2500/32* (2013.01); *C12N 2500/36* (2013.01); *C12N 2500/38* (2013.01); *C12N 2501/115* (2013.01); *C12N 2501/12* (2013.01); *C12N 2501/135* (2013.01); *C12N 2501/15* (2013.01); *C12N 2501/39* (2013.01)

(58) Field of Classification Search
None
See application file for complete search history.

(56) References Cited

U.S. PATENT DOCUMENTS

| | | | |
|---|---|---|---|
| 6,617,159 | B1 | 9/2003 | Cancedda et al. |
| 7,109,032 | B2 * | 9/2006 | Cancedda et al. ............ 435/404 |
| 7,169,610 | B2 | 1/2007 | Brown |
| 2003/0143737 | A1 | 7/2003 | Morrison et al. |
| 2003/0211604 | A1 | 11/2003 | Brown |
| 2005/0032122 | A1 | 2/2005 | Hwang et al. |
| 2005/0090002 | A1 | 4/2005 | Cancedda et al. |
| 2005/0132426 | A1 | 6/2005 | Morrison et al. |
| 2005/0265980 | A1 | 12/2005 | Chen et al. |
| 2005/0272152 | A1 | 12/2005 | Xu et al. |
| 2006/0216821 | A1 | 9/2006 | Totey et al. |
| 2007/0275463 | A1 | 11/2007 | Brown |
| 2009/0202654 | A1 * | 8/2009 | Nixon ..................... 424/574 |
| 2010/0279412 | A1 | 11/2010 | Kato et al. |

FOREIGN PATENT DOCUMENTS

| | | |
|---|---|---|
| EP | 0 274 445 B1 | 7/1993 |
| EP | 1 988 159 A1 | 11/2008 |
| JP | 08-308561 | 11/1996 |
| JP | 09-191874 | 7/1997 |
| JP | 2002-529071 | 9/2002 |
| JP | 2003-516141 | 5/2003 |
| JP | 2005/515777 | 6/2005 |
| JP | 2007-000077 A | 1/2007 |
| JP | 2007-536935 A | 12/2007 |
| KR | 10-2008-00918 09 | 10/2008 |
| WO | 97/34614 | 9/1997 |
| WO | 99/47163 A2 | 9/1999 |
| WO | 03/104442 | 12/2003 |
| WO | 2004/069172 A2 | 8/2004 |
| WO | 2007/080919 A1 | 7/2007 |
| WO | 2009/114860 A2 | 9/2009 |

OTHER PUBLICATIONS

Doucet C. et al (2005), J. Cell. Physiol, vol. 205, No. 2, pp. 228-236.*
Yamaji et al (1998), The Society of Chemical Engineers Muroran Taikai Kenkyu Happyo Koen Yoshishu, p. 140.*
Lee et al. (2004) Blood 103: 1669-1675.*
Gregory et al. (2005) J. Biol. Chem. 280: 2309-2323.*
European Search Report for corresponding Application No. 07706579.5 dated Apr. 2, 2009.
Forte Giancarlo et al.; "Hepatocyte growth factor effects on mesenchymal stem cells: proliferation, migration, and differentiation"; Stem Cells; Jan. 2006, vol. 24, No. 1; pp. 23-33.
International Search Report for corresponding Application No. PCT/JP2007/050232 mailed Mar. 20, 2007.
Christine Doucet et al.; "Platelet Lysates Promote Mesenchymal Stem Cell Expansion: A Safety Substitute for Animal Serum in Cell-Based Therapy Applications"; Journal of Cellular Physiology; 205(2); pp. 228-236; 2005.
Hideki Yamaji et al.; "Promoting effect of phospholipid on proliferation of CHO cells in serum free culturing"; Abstracts of Presentations for the Muroran Meeting of the Society of Chemical Engineering, Japan, at Muroran Institute of Technology, Aug. 6-7, 1998; p. 140. (Includes partial English translation).
Regina Labitzke et al.; "A serum-free medium formulation supporting growth of human umbilical cord vein endothelial cells in long-term cultivation"; Cytotechnology, 35; pp. 87-92; 2001.
Emily Shacter; "Serum-free medium for growth factor-dependent and —independent plasmacytomas and hybridomas"; Journal of Immunological Methods, 99; pp. 259-270; 1987.
Chiyo Hori et al.; "Induction of lithium ion of multiplication of mouse mammory epithelium in culture"; Proc. Natl Acad. Sci. USA; vol. 76, No. 6; pp. 2823-2827; Jun. 1979.
Kentaro Sakai et al.; "Use of Nonionic Surfactants for Effective Supply of Phosphatidic Acid in Serum-Free Culture of Chinese Hamster Ovary Cells"; Journal of Bioscience and Bioengineering; vol. 92, No. 3; pp. 256-261; 2001.

(Continued)

*Primary Examiner* — Michael Pak
(74) *Attorney, Agent, or Firm* — Renner, Otto, Boisselle & Sklar, LLP

(57) ABSTRACT

Disclosed are: a culture medium containing a specific growth factor and at least one phospholipid; a composition for preparation of the culture medium; a kit; and a method. A technique can be provided which uses a serum-free or low-serum culture medium and has a promoting effect on the proliferation of an animal cell comparable to the promoting effect obtained by the culture in a serum-containing culture medium.

8 Claims, 16 Drawing Sheets

(56) References Cited

OTHER PUBLICATIONS

Yoshiro Saito et al.; "III-14 Research on Effect of Essential Micronutrient Selenium on Cell Survival"; Proceedings of the Japanese Conference on the Biochemistry of Lipids; vol. 45; pp. 262-265; 203. (Includes partial English translation).
Ben J. Walth et al.; "Multiplication of Human Diploid Fibroblasts in a Synthetic Medium Supplemented with EGF; Insulin, and Dexamethoasone"; Experimental Cell Research, 134; pp. 303-311; 1981.
Chiyo Hori et al.; "Induction of lithium ion of multiplication mouse mammary epithelium in culture"; Proc. Natl Acad. Sci. USA; vol. 76, No. 6; pp. 2823-2827; Jun. 1979. (Previosly submitted with application on Jul. 10, 2008.
Yoshiro Saito et al.; "III-14 Research on Effect of Essential Micronutrient Selenuim on Cell Survival"; Proceedings of the Japanese Conference on the Biochemistry of Lipids; vol. 45; pp. 262-265; 2003. (Includes English translation). (Previously submitted with application on Jul. 10, 2008).
Korean Office Action for corresponding Korean Application No. 10-2008-7019812 dated Oct. 11, 2010 (with English translation).
Sandstorm et al., "Review: Serum-Free Media for Cultures of Primitive and Mature Hematopoietic Cells", Biotechnology and Bioengineering, 1994, vol. 43, pp. 706-733.
International Search Report for corresponding International Application No. PCT/JP2011/055683 mailed Apr. 5, 2011.
Form PCT/ISA/237 for corresponding International Application No. PCT/JP2011/055683 dated Apr. 5, 2011.
Y Kato, "Development of Serum-free Medium for Human Mesenchymal Stem Cells", Iryokiki Forum (Medical Equipment Forum), 33-35, 2007 and full English translation.
Armand Keating, "How Do Mesenchymal Stromal Cells Suppress T Cells?", Cell Stem Cell, 2, pp. 106-108, 2008.
Corcione et al., "Human mesenchymal stem cells modulates B-cell functions" Blood 107, pp. 367-372, 2008.
Ramasamy et al., "Mesenchymal Stem Cells Inhibit Dendritic Cell Differentiation and Function by Preventing Entry Into the Cell Cycle", Transplantation 83, No. 1, pp. 71-76, 2007.
Aggarwal et al., "Human mesenchymal stem cells modulate allogeneic immune cell responses", Blood 105, pp. 1815-1822, 2005.
Le Blanc et al., "Immunomodulation by mesenchymal stem cells and clinical experience", Journal of Internal Medicine, 262, pp. 509-525, 2007.
Djouad et al., "Immunosuppressive effect of mesenchymal stem cells favors tumor growth in allogeneic animals", Blood 102, pp. 3837-8344, 2003.
Y. Kato, "Active Stemness Molecular Mechanism of Mesenchymal Stem Cells in Serum-free Medium: Diversion from serum regenerative medicine to serum-free regenerative medicine", Research Council Meeting of Japan Society of Plastic and Reconstructive Surgery, 2009, vol. 18$^{th}$, pp. 54-55 and full English translation.
Sawada et al., "Gene Expression Changes in Human Bone-marrow Derived Mesenchymal Stem Cells during the in vitro Culture-Influence of Serum-free Medium", Regenerative Medicine, 2009, vol. 8, No. suppl, p. 248 and full English translation.
Sotiropoulou et al., "Characterization of the Optical Culture Conditions for Clinical Scale Production of Human Mesenchymal Stem Cells", Stem Cells, 2006, vol. 24, pp. 462-471.
Di Nicola et al., "Human bone marrow stromal cells suppress T-lymphocyte proliferation induced by cellular or nonspecific mitogenic stimuli", Blood, 2002, vol. 99, No. 10, pp. 3838-3843.
International Search Report for corresponding International Application No. PCT/JP2009/005573 mailed Dec. 15, 2009.
Form PCT/ISA/237 for International Application No. PCT/JP2009/005573 dated Dec. 15, 2009.
Kratchmarova et al., "Mechanism of Divergent Growth Factor Effects in Mesenchymal Stem Cell Differentiation", Science (2005), vol. 308, p. 1472-1477.
Misawa et al., "Haisei Kensaibo o Mochiita Hone Saisei", Organ Biology (2005), vol. 12, No. 4, pp. 281-289 with machine translation.
Campagnoli et al., "Identification of mesenchymal stem/progenitor cells in human first-trimester fetal blood, liver, and bone marrow", Blood (2001), vol. 98, No. 8, p. 2396-2402.
Supplementary European Search Report for corresponding European Application No. EP 09 82 5870 mailed Mar. 21, 2012.
Kotev-Emeth et al., "Establishment of a Rat Long-Term Culture Expressing the Osteogenic Phenotype: Dependence on Dexamethasone and FGF-2", Connective Tissue Research, 2002, vol. 43, pp. 606-612.
Maegawa et al., "Enhancement of osteoblastic differentiation of mesenchymal stromal cells cultured by selective combination of bone morphogenetic protein-2 (BMP-2) and fibroblast growth factor-2 (FGF-2)", Journal of tissue engineering and regenerative medicine, 2007, vol. 1, pp. 306-313.
Chaudhary et al., "Differential growth factor control of bone formation through osteoprogenitor differentiation", Bone, 2004, vol. 34, pp. 402-411.
Frank et al., "Real-Time Quantitative RT-PCR Analysis of Human Bone Marrow Stromal Cells During Osteogenic Differentiation in Vitro", Journal of Cellular Biochemistry, 2002, vol. 85, pp. 737-746.
Friedman et al., "Osteogenic Differentiation of Human Mesenchymal Stem Cells is Regulated by Bone Morphogenetic Protein-6", Journal of Cellular Biochemistry, 2006, vol. 98, pp. 538-554.
US Office Action dated Oct. 2, 2012 for corresponding U.S. Appl. No. 13/127,774.
Summons to Attend Oral Proceedings Pursuant to Rule 115(1) EPC for corresonding Application No. EP 07706579.5 dated Oct. 25, 2012.
GIBCO Invitrogen Cell Culture. StemPro Osteogenesis Differentiation Kit. 2008.
Shioi et al., "β-Glycerophosphate Accelerates Calcification in cultured Bovine Vascular Smooth Muscle Cells", Arteriosclerosis, Thrombosis, and Vascular Biology, 1995; 15:2003-2009.
Office Action dated Feb. 27, 2013 from co-pending U.S. Appl. No. 13/127,774.
Extended European Search Report dated Aug. 2, 2013 in European Application No. 11753445.3, corresponding to co-pending U.S. Appl. No. 13/583,150.
Office Action dated Jul. 22, 2013 in copending Application No. 13/583,150.
Burns et al., "Tumorigenic Heterogeneity in Cancer Stem Cells Evolved from Long-term Cultures of Telomerase-Immortalized Human Mesenchymal Stem Cells", Cancer Research 65(8): pp. 3126-3135, Apr. 15, 2005.
Clyman et al., "Integrin receptors on aortic smooth muscle cells mediate adhesion to fibronectin, laminin, and collagen", Circulation Research, vol. 67, No. 1, pp. 175-186, Jul. 1990.
Kao et al., "TrypZean™: Recombinant Bovine Trypsin Expressed in Corn—A Non-animal Alternative", SIGMA® Technical Articles, available online, two pages, published Jan. 2004.
Advisory Action dated May 10, 2013 from co-pending U.S. Appl. No. 13/127,774.
Office Action dated Apr. 11, 2013 from co-pending U.S. Appl. No. 13/583,150.
Office Action for co-pending Korean Application No. 10-2012-7026184 dated Nov. 29, 2013, with English translation.
Lee et al., "Tumorigenesis Study of Canine Adipose Derived-mesenchymal Stem Cell", Journal of Toxicology and Public Health, Sep. 2007, vol. 23, No. 3, pp. 271-278, with English translation.
Yañez et al., "Adipose Tissue-Derived Mesenchymal Stem Cells Have in Vivo Immunosuppressive Properties Applicable for the Control of the Graft-Versus-Host Disease", Stem Cells, 2006, vol. 24, pp. 2582-2591.
Final Office Action for co-pending U.S. Appl. No. 13/583,150 dated Dec. 18, 2013.
Office Action for co-pending U.S. Appl. No. 13/127,774 dated Dec. 6, 2013.
Valta et al., "Regulation of Osteoblast Differentiation: A Novel Function for Fibroblast Growth Factor 8", Endocrinology, May 2006, 147(5), pp. 2171-2182.
Broedel, Jr. et al., "The Case for Serum-Free Media", BioProcess International, Feb. 2003, pp. 56-58.

(56) References Cited

OTHER PUBLICATIONS

Singh et al., "Parathyroid Hormone Stimulates Phosphatidylethanolamine Hydrolysis by Phospholipase D in Osteoblastic Cells", Lipids, Nov. 2005, 40(11), pp. 1135-1140.
Pasco et al., "Antioxidant Vitamin Supplements and Markers of Bone Turnover in a Community Sample of Nonsmoking Women", Journal of Women's Health, 2006, 15(3), pp. 295-300.
Neuss et al., "Functional Expression of HGF and HFG Receptor/c-met in Adult Human Mesenchymal Stem Cells Suggests a Role in Cell Mobilization, Tissue Repair, and Wound Healing", Stem Cells, 2004, 22, pp. 405-414.
Peter et al., "Osteoblastic Phenotype of Rat Marrow Stromal Cells Cultured in the Presence of Dexamethasone, β-Glycerolphosphate, and L-ascorbic acid", Journal of Cellular Biochemistry, 71, 1998; pp. 55-62.
Office Action dated Dec. 19, 2014 for co-pending U.S. Appl. No. 13/127,774.
Chen et al., "Extracellular Matrix Made by Bone Marrow Cells Facilitates Expansion of Marrow-Derived Mesenchymal Progenitor Cells and Prevents Their Differentiation Into Osteoblasts", Journal of Bone and Mineral Research, vol. 22, No. 12, 2007, pp. 1943-1956.
Office Action dated Jan. 26, 2014 for co-pending U.S. Appl. No. 13/583,150.
Advisory Action for co-pending U.S. Appl. No. 13/583,150 dated Mar. 3, 2014.
Final Office Action for co-pending U.S. Appl. No. 13/127,774 dated May 8, 2014.
Advisory Action dated Jul. 31, 2014 from co-pending U.S. Appl. No. 13/127,774.

* cited by examiner

F I G. 2
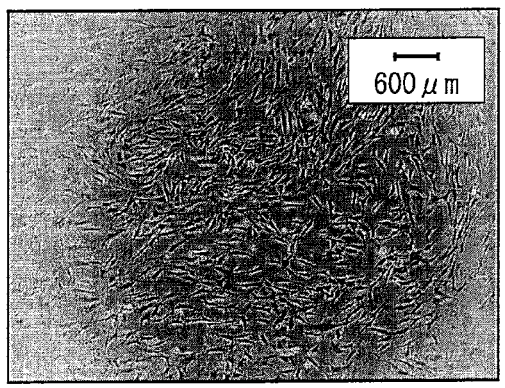
CULTURE MEDIUM 2
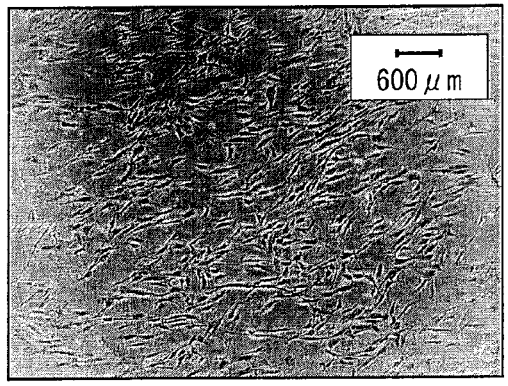
CULTURE MEDIUM 3
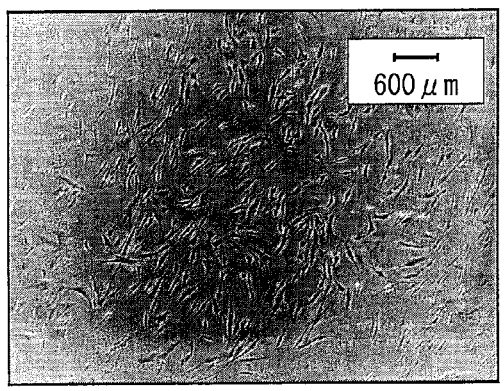
CULTURE MEDIUM 3-3
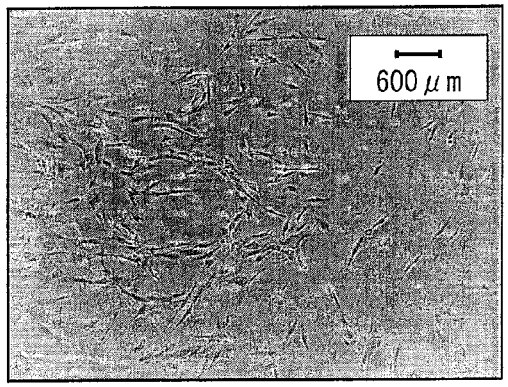
CULTURE MEDIUM 3-2
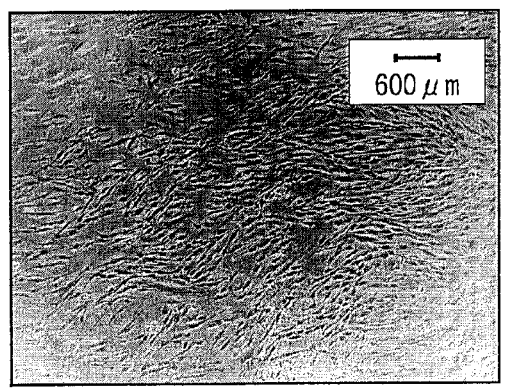
CULTURE MEDIUM 4

FIG. 3
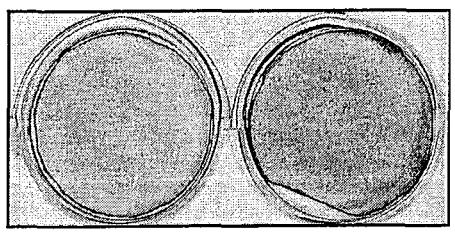 CULTURE MEDIUM 2
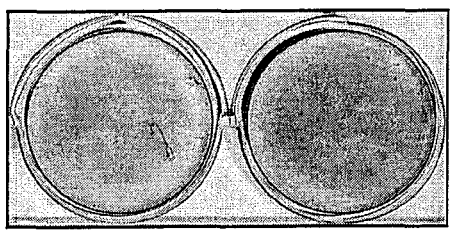 CULTURE MEDIUM 3
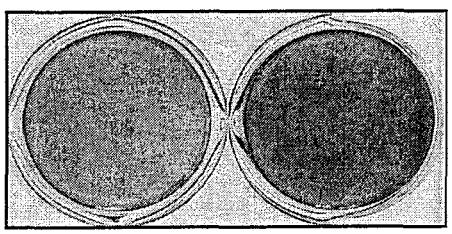 CULTURE MEDIUM 4
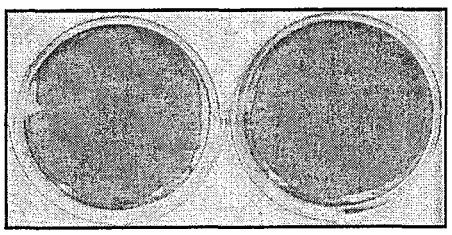 CULTURE MEDIUM 5

F I G. 4
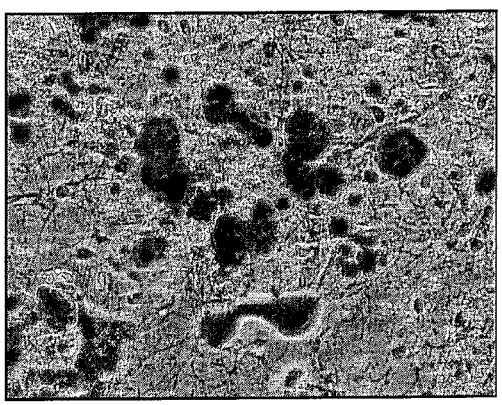
CULTURE MEDIUM 2
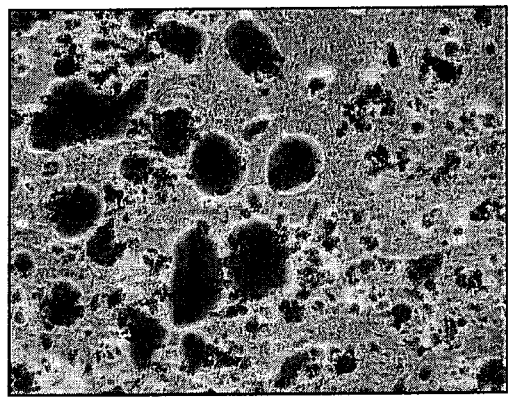
CULTURE MEDIUM 3
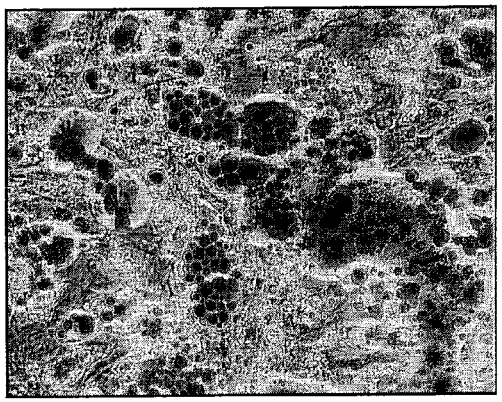
CULTURE MEDIUM 4
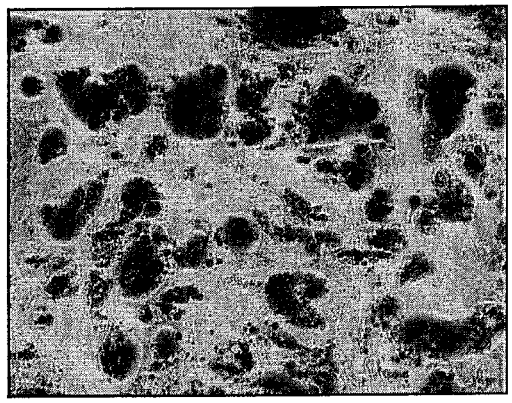
CULTURE MEDIUM 5

FIG. 6
CULTURE MEDIUM 2
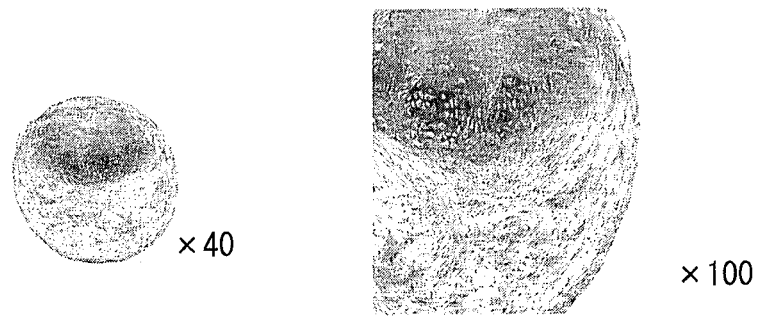
CULTURE MEDIUM 4-2
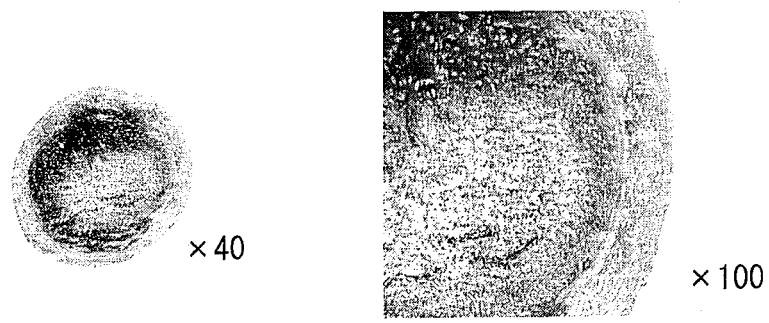

D : Dexamethasone
E : EGF
F : bFGF
G : PDGF
H : HGF
I : Insulin
J : TGF-β3
T : Transferrin A1 : Arachidonic acid
A2 : Linoleic acid
A3 : Linolenic acid
A4 : Oleic acid
A5 : B1(CD)
A6 : Phosphatidic acid (PA)
A7 : Phosphatidylcholine (PC)

FIG. 13

| | Source | Effective concentration | Optimum concentration |
|---|---|---|---|
| BASAL MEDIUM | | | |
| DMEM/MCDB201 | Sigma: D6046/M6770 | 1:1 | |
| Supplement A (BASAL FACTOR) | | | |
| (human recombinant) Basic fibroblast growth factor (bFGF) | Pepro Tech: 100-18B | 0.1~100 ng/ml | 3 ng/ml |
| Dexamethasone (Dex) | Sigma: D1756 | $10^{-6} \sim 10^{-10}$ M | $10^{-8}$ M |
| (human recombinant) Insulin | Wako: 090-03446 | 0.5~50 $\mu$g/ml | 6.25 $\mu$g/ml |
| Transferrin | Sigma: T0665 | 0.5~50 $\mu$g/ml | 6.25 $\mu$g/ml |
| Selenous acid | Sigma: 21,117-6 | 0.1~50 $\mu$g/ml | 6.25 $\mu$g/ml |
| Bovine serum albumin (BSA) | Sigma: A8806 | 0.1~50 mg/ml | 1.25 mg/ml |
| Supplement B-1 (BASAL LIPID 1) | | | |
| Chemically defined lipid concentrate (CD) | Gibco: 11905-031 | 1/1000~1/10 | 1/100 |
| (CONCENTRATION OF STOCK SOLUTION : Arachidonic Acid 2.0 $\mu$g/ml, Cholesterol 220.00 $\mu$g/ml, DL-$\alpha$-Tocopherol-Acetate 70.00 $\mu$g/ml, Linoleic Acid 540.00 $\mu$g/ml, Linolenic Acid 10.00 $\mu$g/ml, Myristic Acid 10.00 $\mu$g/ml, Oleic Acid 10.00 $\mu$g/ml, Palmitoleic Acid 10.0 $\mu$g/ml, Palmitic Acid 10.0 $\mu$g/ml, Stearic Acid 10.00 $\mu$g/ml) | | | |
| Supplement B-2 (BASAL LIPID 2) | | | |
| Lecithin from Soybean (LS) | Waco: 120-00832 | 0.5~50 $\mu$g/ml | 10 $\mu$g/ml |
| cholesterol lipid concentrate (chol) | Gibco: 12531-018 | 0.1~30 $\mu$g/ml | 3 $\mu$g/ml |
| (+$\alpha$)-Tocopherol-Acetate (VE) | Sigma: T1157 | 0.1~50 $\mu$g/ml | 2 $\mu$g/ml |
| Supplement C | | | |
| (human recombinant) Hepatocyte growth factor (HGF) | Sigma: H1404 | 0.1~50 ng/ml | 5 ng/ml |
| (human recombinant) Transforming growth factor-$\beta_3$ (TGF-$\beta_3$) | Pepro Tech: 100-36 | 0.5~100 ng/ml | 10 ng/ml |
| (human recombinant) Platelet derived growth factor (PDGF-BB) | Waco: 160-19741 | 0.5~100 ng/ml | 10 ng/ml |
| Others | | | |
| (human recombinant) Epidermal growth factor (EGF) | Waco: 050-07141 | 0.5~200 ng/ml | 20 ng/ml |
| Ascorbic acid (VC) | Sigma: A8960 | 0.5~200 $\mu$g/ml | 50 $\mu$g/ml |
| Phosphatidylcholine (PC) | Wako: 163-21181 | 0.5~100 $\mu$g/ml | 10 $\mu$g/ml |
| Phosphatidic acid sodium salt (PA) | Sigma: P9511 | 0.5~100 $\mu$g/ml | 10 $\mu$g/ml |
| (human recombinant) Vascular Endothelial Growth Factor (VEGF) | Sigma: V3388 | 0.5~100 ng/ml | 10 ng/ml |
| (human recombinant) Connective Tissue Growth Factor (CTGF) | Wako: 036-19471 | 0.1~20 $\mu$g/ml | 1 $\mu$g/ml |

FIG. 14

| | Source | Effective concentration | Optimum concentration |
|---|---|---|---|
| *BASAL MEDIUM* | | | |
| DMEM/MCDB201 | Sigma: D6046/M6770 | | |
| +L-glutamine | Sigma: G3126 | | 2 mM |
| *Supplement A (BASAL FACTOR)* | | | |
| (human recombinant) Basic fibroblast growth factor (bFGF) | Pepro Tech: 100-18B | 0.1~100 ng/ml | 3 ng/ml |
| Dexamethasone (Dex) | Sigma: D1756 | $10^{-6} \sim 10^{-10}$ M | $10^{-8}$ M |
| (human recombinant) Insulin | Wako: 090-03446 | 0.1~50 μg/ml | 6.25 μg/ml |
| Transferrin | Sigma: T0665 | 0.1~50 μg/ml | 6.25 μg/ml |
| Selenous acid | Sigma: 21,117-6 | 0.1~50 μg/ml | 6.25 μg/ml |
| Bovine serum albumin (BSA) | Sigma: A8806 | 0.1~50 mg/ml | 1.25 mg/ml |
| *Supplement B-1 (BASAL LIPID 1)* | | | |
| Chemically defined lipid concentrate (CD) | Gibco: 11905-031 | 1/1000~1/50 | 1/100 |
| (COMPOSITION : Arachidonic Acid 2.0 μg/ml, Cholesterol 220.00 μg/ml, DL-α-Tocopherol-Acetate 70.00 μg/ml, Linoleic Acid 10.00 μg/ml, Linolenic Acid 10.00 μg/ml, Myristic Acid 10.00 μg/ml, Oleic Acid 10.00 μg/ml, Palmitoleic Acid 10.0 μg/ml, Palmitic Acid 10.0 μg/ml, Pluronic F-68 100,000.00 μg/ml, Stearic Acid 10.00 μg/ml, Tween 80 2,200.00 μg/ml) | | | |
| *Supplement B-2 (BASAL LIPID 2)* | | | |
| Lecithin from Soybean (LS) | Waco: 120-00832 | 0.5~50 μg/ml | 10 μg/ml |
| Cholesterol lipid concentrate (Chol) | Gibco: 12531-018 | 1/1000~1/50 | 1/500 |
| (+α)-Tocopherol-Acetate (VE) | Sigma: T1157 | 0.1~50 μg/ml | 2 μg/ml |
| *Supplement C* | | | |
| (human recombinant) Hepatocyte growth factor (HGF) | Sigma: H1404 | 0.5~100 ng/ml | 10 ng/ml |
| (human recombinant) Transforming growth factor-β3 (TGF-β3) | Pepro Tech: 100-36 | 0.5~100 ng/ml | 10 ng/ml |
| (human recombinant) Platelet derived growth factor (PDGF-BB) | Waco: 160-19741 | 0.5~100 ng/ml | 10 ng/ml |
| *Others* | | | |
| (human recombinant) Epidermal growth factor (EGF) | Waco: 050-07141 | 0.5~100 ng/ml | 20 ng/ml |
| Ascorbic acid 2-phosphate sesquimagnesium salt (VC) | Sigma: A8960 | 5~200 μg/ml | 50 μg/ml |
| Phosphatidylcholine (PC) | Wako: 163-21181 | 0.5~100 μg/ml | 10 μg/ml |
| Phosphatidic acid sodium salt (PA) | Sigma: P9511 | 0.5~100 μg/ml | 10 μg/ml |

F I G. 16 (a)
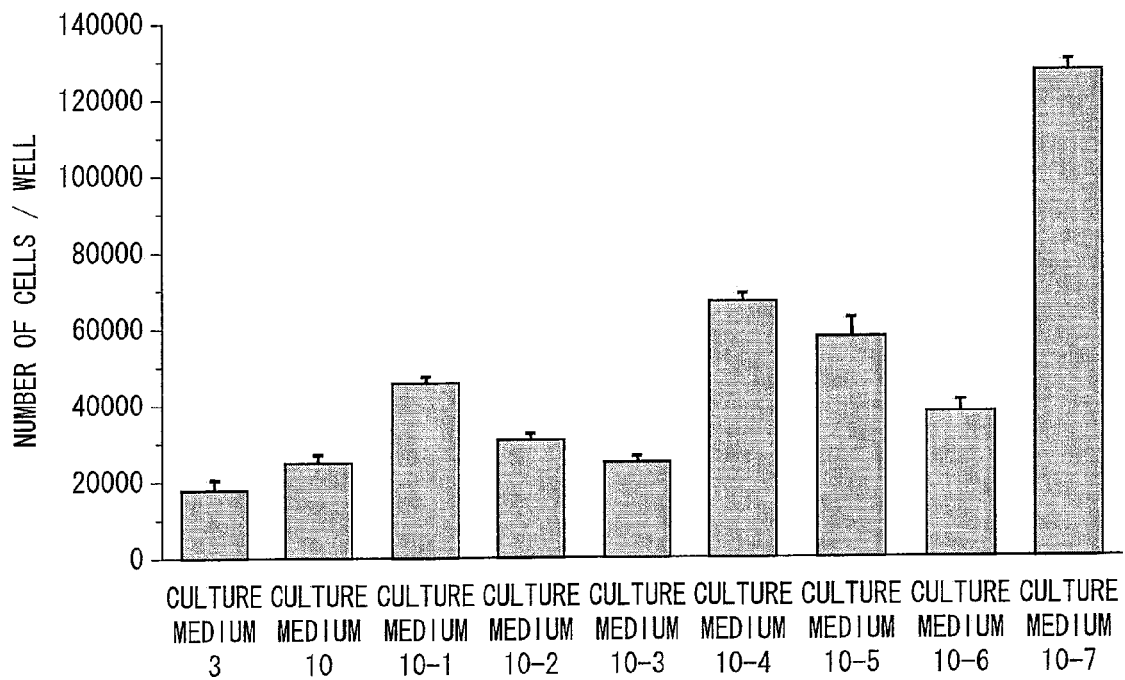
F I G. 16 (b)
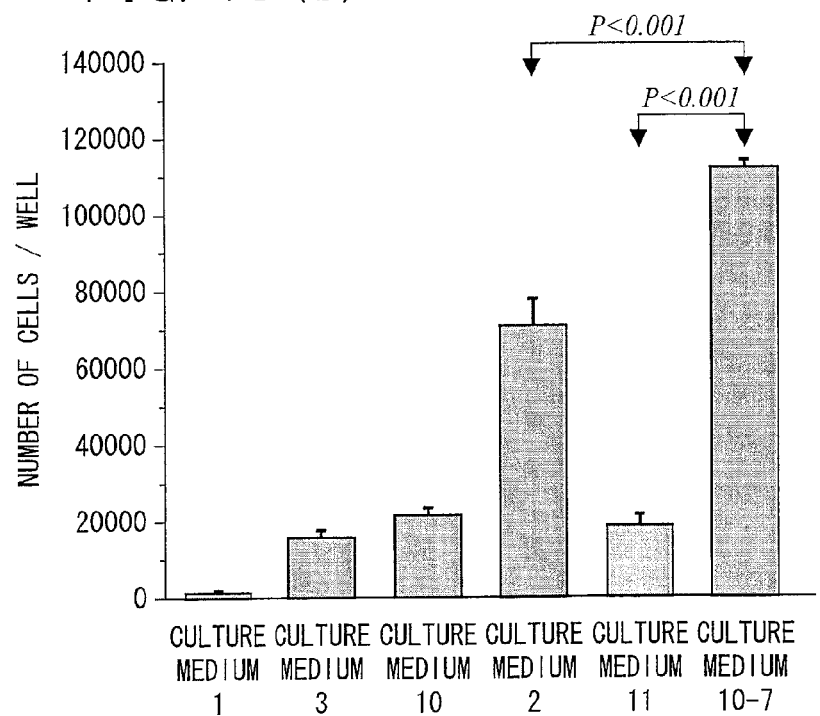

CULTURE MEDIUM ADDITIVE FOR USE IN SERUM-FREE CULTURING OF ANIMAL CELL, KIT AND USE THEREOF

TECHNICAL FIELD

The present invention relates to a composition to be added to a culture medium for culturing of an animal cell, a kit, and a use thereof. More specifically, the present invention relates to a composition for culturing an animal cell under a serum-free condition or a low-serum condition, a kit, and a use thereof.

BACKGROUND ART

A mesenchymal stem cell is one type of somatic stem cells and present in tissues of bone marrow or the like. A mesenchymal stem cell is known as a stem cell having a pluripotency to differentiate into an adipose cell, a bone cell, a chondrocyte, or the like, and having a self-propagating potential. Currently, the mesenchymal stem cell is used as a cell for transplantation in regenerative medicine field. The mesenchymal stem cell is applied to various diseases such as bone defect, cartilage defect, periodontal disease, myocardial infarction, refractory cutaneous disease, osteoporosis, osteoarthrosis, spinal cord injury, hematopoietic support, and antirejection in organ transplantation. It is expected that the mesenchymal stem cell will be applied to more and more diseases in the future (for example, cerebral infarction, arteriosclerosis obliterans, kidney disorder, and the like).

The mesenchymal stem cell is present in tissues of bone marrow, periostea, or the like. Mesenchymal stem cells taken from such tissues are proliferated and further differentiated into intended cells, so that tissues that can be used in tissue regeneration medicine are prepared. However, since the number of mesenchymal stem cells present in living tissues is little, the use of the mesenchymal stem cells for transplantation requires sufficient proliferation of the cells taken from tissues.

Generally, culturing of animal cells is carried out with the use of a culture medium to which 5 to 20% nonhuman animal-derived serum such as fetal bovine serum or the like is added. The serum is used as a nutrient source for promoting in vitro cell growth and/or proliferation, or a resource for a biologically active substance such as hormone or the like. However, serum is very expensive, and components of serum differ lot by lot because the serum is a natural product. Moreover, it is necessary to purify cultured cells by removing serum-derived proteins or the like from the cultured cells, thereby causing a complicated process. Furthermore, there is a risk that cultured cells are infected with unknown pathogen (such as virus, pathological prion, or the like) that is contained in serum.

Meanwhile, techniques for culturing animal cells without using nonhuman animal-derived serum have been developed. For example, culture of cells used for autologous transplantation treatment (in which cells taken from a patient are cultured and the cultured cells are transplanted to the patient) uses autologous human serum obtained from the same patient. This avoids contamination of cultured cells. However, large amounts of blood are required for producing serum, which gives heavy burden to patients.

In order to avoid the problems, a culture medium that contains no serum (serum-free culture medium) or a culture medium whose content of serum is low (low-serum culture medium) has been developed. Low serum concentration in a culture medium decreases a proliferation ability of cells remarkably decreases or kills the cells. From this reason, in order to produce a culture medium which is capable of culturing cells without losing its proliferation property, it is necessary to add in a culture medium a cell growth factor alternative to serum. Conventionally, a variety of peptide hormones, growth factors or the like are used as a cell growth factor alternative to serum (for example, see Patent Documents and 2). As such a serum-free culture medium, for example, a serum-free culture medium, which uses a HAM's F12 culture medium as a basal medium, and in which insulin, transferrin, and the like is added, is known.

Another known method is a method in which chondrocyte to be used in medical treatment is cultured in a serum-free culture medium in which a fatty acid is added in addition to a growth factor (for example, see Patent Documents 3 and 4). Furthermore, Patent Document 5 discloses a method for culturing a neural stem cell for long periods and its composition.

[Patent Document 1]
Japanese Unexamined Patent Publication, Tokukaihei, No. 8-308561 (published on Nov. 26, 1996)

[Patent Document 2]
Japanese Unexamined Patent Publication, Tokukaihei, No. 9-191874 (published on Jul. 29, 1997)

[Patent Document 3]
Japanese Translation of PCT international application, Tokuhyo, No. 2005-515777 (published on Jun. 2, 2005)

[Patent Document 4]
Japanese Translation of PCT international application, Tokuhyo, No. 2002-529071 (published on Sep. 10, 2002)

[Patent Document 5]
Japanese Translation of PCT international application, Tokuhyo, No. 2003-516141 (published on May 13, 2003)

DISCLOSURE OF INVENTION

However, even the use of the aforementioned culture media cannot facilitate the cell proliferation sufficiently compared with the use of the culture medium containing 10% of serum. Especially, in the conventional techniques, it is difficult to carry out long-term culturing, which is necessary for large-scale culturing.

The present invention is achieved in view of the above problems. An object of the present invention is to provide a technique that uses a serum-free culture medium and can facilitate animal cell proliferation comparable to that of a culture medium containing 10% serum.

For use in serum-free culturing of an animal cell, a culture medium additive of the present invention contains: at least three growth factors selected from the group consisting of FGF, PDGF, TGF-$\beta$, and HGF; and at least one phospholipid.

In the culture medium additive of the present invention, it is preferable that the phospholipid is selected from the group consisting of phosphatidic acid, lysophosphatidic acid, phosphatidylinositol, phosphatidylserine, phosphatidylethanolamine, phosphatidyl choline, and phosphatidylglycerol.

It is preferable that the culture medium additive of the present invention further contain at least one fatty acid.

In the culture medium additive of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive of the present invention may further contain cholesterol.

The culture medium additive of the present invention may further contain at least two factors selected from the group consisting of EGF, CTGF, VEGF, and ascorbic acid compound.

The culture medium additive of the present invention may further contain a lipid oxidation inhibitor.

In the culture medium additive of the present invention, although it is preferable that the lipid oxidation inhibitor be DL-α-tocopherol acetate (vitamin E), L-glutathione, or 2-mercaptoethanol, other reducing agent may be also used.

The culture medium additive of the present invention may further contain lithium chloride.

The culture medium additive of the present invention my further contain a surfactant.

In the culture medium additive of the present invention, it is preferable that the surfactant be Pluronic F-68 or Tween-80, but other surfactant may be also used.

The culture medium additive of the present invention may further contain insulin, transferrin, and selenate.

The culture medium additive of the present invention may further contain dexamethasone, or other glucocorticoid.

In the culture medium additive of the present invention, it is preferable that the animal cell be an undifferentiated cell.

In the culture medium additive of the present invention, it is preferable that the animal cell be a mesenchymal stem cell.

In the culture medium additive of the present invention, it is preferable that the animal cell be a cell (for example, a monkey kidney-derived COS cell) that is nearly in an undifferentiated state because a specified differentiation potential is lost.

For use in serum-free culturing of an animal cell, a culture medium of the present invention contains compositions of the culture medium additive.

For use in serum-free culturing of an animal cell, a culture method of the present invention includes the step of culturing an animal cell in the culture medium.

For use in serum-free culturing of an animal cell, a culture medium additive kit of the present invention includes the culture medium additive.

For use in serum-free culturing of an animal cell, the culture medium additive kit of the present invention includes separately: at least three growth factors selected from the group consisting of FGF, PDGF, TGF-β, and HGF; and at least one phospholipid.

It is preferable that the culture medium additive kit of the present invention include at least one fatty acid.

In the culture medium additive kit of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive kit of the present invention, it is preferable that the fatty acid be selected from the group consisting of linoleic acid, oleic acid, linolenic acid, arachidonic acid, myristic acid, palmitoyl acid, palmitic acid, and stearic acid.

The culture medium additive kit of the present invention may further include cholesterol.

The culture medium additive kit of the present invention may further include at least two factors selected from the group consisting of EGF, CTGF, VEGF, and ascorbic acid compound.

The culture medium additive kit of the present invention may further include a lipid oxidation inhibitor.

In the culture medium additive kit of the present invention, it is preferable that the lipid oxidation inhibitor be DL-α-tocopherol acetate (vitamin E), L-glutathione, or 2-mercaptoethanol, but other reducing agent may be also used.

The culture medium additive kit of the present invention may further include lithium chloride.

The culture medium additive kit of the present invention may further include a surfactant.

In the culture medium additive kit of the present invention, it is preferable that the surfactant be Pluronic F-68 or Tween-80, but other surfactant may also used.

The culture medium additive kit of the present invention may further include insulin, transferrin, and selenate.

The culture medium additive kit of the present invention may further include dexamethasone, or other glucocorticoid.

In the culture medium additive kit of the present invention, it is preferable that the animal cell be an undifferentiated cell.

In the culture medium additive kit of the present invention, it is preferable that the animal cell be a mesenchymal stem cell.

In the culture medium additive kit of the present invention, it is preferable that the animal cell be a cell (for example, a monkey kidney-derived COS cell) that is nearly in an undifferentiated state because a specified differentiation potential is lost.

For use in serum-free culturing of an animal cell, a culture medium of the present invention contains components included in the culture medium additive kit.

For use in serum-free culturing of an animal cell, a culture method of the present invention includes the step of culturing an animal cell in the culture medium.

For use in serum-free culturing of an animal cell, a culture method of the present invention includes the step of adding to a basal medium simultaneously: at least three growth factors selected from the group consisting of FGF, PDGF, TGF-β, and HGF; and at least one phospholipid.

It is preferable that the culture method of the present invention include the step of further adding at least one fatty acid to the basal medium.

In order that a stem cell is continuously subcultured while maintaining its differentiation potential, a culture medium additive of the present invention contains: at least three growth factors selected from the group consisting of FGF, PDGF, TGF-β, and HGF; and at least one phospholipid.

It is preferable that the culture medium additive of the present invention further contain at least one fatty acid.

In order that a stem cell is continuously subcultured while maintaining its differentiation potential, a culture medium additive kit of the present invention includes: at least three growth factors selected from the group consisting of FGF, PDGF, TGF-β, HGF; and at least one phospholipid.

It is preferable that the culture medium additive kit of the present invention further include at least one fatty acid.

A culture medium of the present invention contains: at least three growth factors selected from the group consisting of FGF, PDGF, TGF-β, and HGF; and at least one phospholipid.

It is preferable that the culture medium of the present invention further contain at least one fatty acid.

In order that a stem cell is continuously subcultured while maintaining its differentiation potential, a culture method of the present invention includes the step of adding to a basal medium simultaneously: at least three growth factors selected from the group consisting of FGF, PDGF, TGF-β, and HGF; and at least one phospholipid.

It is preferable that the culture method of the present invention include the step of further adding to the basal medium at least one fatty acid.

For use in culture of a primary-cultured stem cell, a culture medium additive of the present invention contains: PDGF; at least one phospholipid; at least one fatty acid; and at least two factors selected from the group consisting of EGF, CTGF, VEGF, and ascorbic acid compound.

The culture medium additive of the present invention may further contain at least one factor selected from the group consisting of FGF, TGF-β, and HGF.

In the culture medium additive of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive of the present invention may further contain cholesterol.

The culture medium additive of the present invention may further contain a lipid oxidation inhibitor.

In the culture medium additive of the present invention, it is preferable that the lipid oxidation inhibitor be DL-α-tocopherol acetate (vitamin E).

The culture medium additive of the present invention may further contain a surfactant.

In the culture medium additive of the present invention, it is preferable that the surfactant be Pluronic F-68 or Tween-80, but other surfactant may be also used.

The culture medium additive of the present invention may further contain insulin, transferrin, and selenate.

The culture medium additive of the present invention may further contain dexamethasone or other glucocorticoid.

For use in culture of a primary-cultured stem cell, a culture medium additive kit of the present invention includes: PDGF; at least one phospholipid; at least one fatty acid; and at least two factors selected from the group consisting of EGF, CTGF, VEGF, and ascorbic acid compound.

The culture medium additive kit of the present invention may further include at least one factor selected from the group consisting of FGF, TGF-β, and HGF.

In the culture medium additive kit of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive kit of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive kit of the present invention may further include cholesterol.

The culture medium additive kit of the present invention may further include a lipid oxidation inhibitor.

In the culture medium additive kit of the present invention, it is preferable that the lipid oxidation inhibitor be DL-α-tocopherol acetate (vitamin E).

The culture medium additive kit of the present invention may further include a surfactant.

In the culture medium additive kit of the present invention, it is preferable that the surfactant be Pluronic F-68 or Tween-80, but other surfactant may be also used.

The culture medium additive kit of the present invention may further include insulin, transferrin, and selenate.

The culture medium additive kit of the present invention may further include dexamethasone or other glucocorticoid.

For use in culture of a primary-cultured stem cell, a culture method of the present invention includes the step of adding to a basal medium simultaneously: PDGF; at least one phospholipid; at least one fatty acid; and at least two factors selected from the group consisting of EGF, CTGF, VEGF, and ascorbic acid compound.

The culture method of the present invention may further include the step of adding to the basal medium at least one factor selected from the group consisting of FGF, TGF-β, and HGF.

For use in continuous subculturing of a mouse fibroblast, a culture medium additive of the present invention contains: TGF-β; PDGF; at least one phospholipid; at least one fatty acid; and at least two factors selected from the group consisting of EGF, CTGF, VEGF, and ascorbic acid compound.

The culture medium additive of the present invention may further contain FGF and/or HGF.

In the culture medium additive of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive of the present invention may further contain cholesterol.

The culture medium additive of the present invention may further contain a lipid oxidation inhibitor.

In the culture medium additive of the present invention, it is preferable that the lipid oxidation inhibitor be DL-α-tocopherol acetate (vitamin E).

The culture medium additive of the present invention may further contain a surfactant.

In the culture medium additive of the present invention, it is preferable that the surfactant be Pluronic F-68 or Tween-80, but other surfactant may be also used.

The culture medium additive of the present invention may further contain insulin, transferrin, and selenate.

The culture medium additive of the present invention may further contain dexamethasone or other glucocorticoid.

For use in continuous subculture of a mouse fibroblast, a culture medium additive kit of the present invention includes: TGF-β; PDGF; at least one phospholipid; at least one fatty acid; and at least two factors selected from the group consisting of EGF, CTGF, VEGF, and ascorbic acid compound.

The culture medium additive kit of the present invention may further include FGF and/or HGF.

In the culture medium additive kit of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive kit of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive kit of the present invention may further include cholesterol.

The culture medium additive kit of the present invention may further include a lipid oxidation inhibitor.

In the culture medium additive kit of the present invention, it is preferable that the lipid oxidation inhibitor be DL-α-tocopherol acetate (vitamin E).

The culture additive medium kit of the present invention may further include a surfactant.

In the culture medium additive kit of the present invention, it is preferable that the surfactant be Pluronic F-68 or Tween-80, but other surfactant may be also used.

The culture medium additive kit of the present invention may further include insulin, transferrin, and selenate.

The culture medium additive kit of the present invention may further include dexamethasone or other glucocorticoid.

For use in continuous subculture of a mouse fibroblast, a culture method of the present invention includes the step of adding to a basal medium simultaneously: TGF-β; PDGF; at least one phospholipid; at least one fatty acid; and at least two factors selected from the group consisting of EGF, CTGF, VEGF, and ascorbic acid compound.

The culture method of the present invention may further include the step of adding to the basal medium FGF and/or HGF.

For use in continuous subculture of a Chinese hamster ovary-derived cell, a culture medium additive of the present invention contains: PDGF; at least one phospholipid; at least one fatty acid; and at least two factors selected from the group consisting of EGF, CTGF, VEGF, and ascorbic acid compound.

The culture medium additive of the present invention may further contain at least one factor selected from FGF, TGF-β, and HGF.

In the culture medium additive of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive of the present invention may further contain cholesterol.

The culture medium additive of the present invention may further contain a lipid oxidation inhibitor.

In the culture medium additive of the present invention, it is preferable that the lipid oxidation inhibitor be DL-α-tocopherol acetate (vitamin E).

The culture medium additive of the present invention may further contain a surfactant.

In the culture medium additive of the present invention, it is preferable that the surfactant be Pluronic F-68 or Tween-80, but other surfactant may be also used.

The culture medium additive of the present invention may further contain insulin, transferrin, and selenate.

The culture medium additive of the present invention may further contain dexamethasone or other glucocorticoid.

For use in continuous subculture of a Chinese hamster ovary-derived cell, a culture medium additive kit of the present invention includes: PDGF; at least one phospholipid; at least one fatty acid; and at least two factors selected from the group consisting of EGF, CTGF, VEGF, and ascorbic acid compound.

The culture medium additive kit of the present invention may further include at least one factor selected from the group consisting of FGF, TGF-β, and HGF.

In the culture medium additive kit of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive kit of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive kit of the present invention may further include cholesterol.

The culture medium additive kit of the present invention may further include a lipid oxidation inhibitor.

In the culture medium additive kit of the present invention, it is preferable that the lipid oxidation inhibitor be DL-α-tocopherol acetate (vitamin E).

The culture medium additive kit of the present invention may further include a surfactant.

In the culture medium additive kit of the present invention, it is preferable that the surfactant be Pluronic F-68 or Tween-80, but other surfactant may be also used.

The culture medium additive kit of the present invention may further include insulin, transferrin, and selenate.

The culture medium additive kit of the present invention may further include dexamethasone or other glucocorticoid.

For use in continuous subculturing of a Chinese hamster ovary-derived cell, a culture method of the present invention includes the step of adding to a basal medium simultaneously: a PDGF; at least one phospholipid; at least one fatty acid; and at least two factors selected from the group consisting of EGF, CTGF, VEGF, and ascorbic acid compound.

The culture method of the present invention may further include the step of adding to the basal medium at least one factors selected from the group consisting of FGF, TGF-β, and HGF.

For use in continuous subculture of a human skin-derived fibroblast, a culture medium additive of the present invention contains: FGF; at least one phospholipid; at least one fatty acid; and at least two factors selected from the group consisting of EGF, CTGF, VEGF, and ascorbic acid compound.

The culture medium additive of the present invention may further contain at least one factor selected from the group of TGF-β, HGF, and PDGF.

In the culture medium additive of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive of the present invention may further contain cholesterol.

The culture medium additive of the present invention may further contain a lipid oxidation inhibitor.

In the culture medium additive of the present invention, it is preferable that the lipid oxidation inhibitor be DL-α-tocopherol acetate (vitamin E).

The culture medium additive of the present invention may further contain a surfactant.

In the culture medium additive of the present invention, it is preferable that the surfactant be Pluronic F-68 or Tween-80, but other surfactant may be also used.

The culture medium additive of the present invention may further contain insulin, transferrin, and selenate.

The culture medium additive of the present invention may further contain dexamethasone or other glucocorticoid.

For use in continuous subculturing of a human skin-derived fibroblast, a culture medium additive kit of the present invention includes: FGF; at least one phospholipid; at least one fatty acid; and at least two factors selected from the group consisting of EGF; CTGF; VEGF; and ascorbic acid compound.

The culture medium additive kit of the present invention may further include at least one factor selected from the group consisting of TGF-β, HGF, and PDGF.

In the culture medium additive kit of the present invention, it is preferable that the phospholipid be selected from the group consisting of phosphatidic acid, lysophosphatidic acid, phosphatidylinositol, phosphatidylserine, phosphatidylethanolamine, phosphatidyl choline, and phosphatidylglycerol.

In the culture medium additive kit of the present invention, it is preferable that the fatty acid be selected from the group consisting of linoleic acid, oleic acid, linolenic acid, arachidonic acid, myristic acid, palmitoyl acid, palmitic acid, and stearic acid. The linoleic acid, the linolenic acid, and the arachidonic acid, which are nutritionally-essential fatty acids, are particularly preferable.

The culture medium additive kit of the present invention may further include cholesterol.

The culture medium additive kit of the present invention may further include a lipid oxidation inhibitor.

In the culture medium additive kit of the present invention, it is preferable that the lipid oxidation inhibitor be DL-α-tocopherol acetate (vitamin E).

The culture medium additive kit of the present invention may further include a surfactant.

In the culture medium additive kit of the present invention, it is preferable that the surfactant be Pluronic F-68 or Tween-80, but other surfactant may be also used.

The culture medium additive kit of the present invention may further include insulin, transferrin, and selenate.

The culture medium additive kit of the present invention may further include dexamethasone or other glucocorticoid.

For use in continuous subculturing of human skin-derived fibroblast, a culture method of the present invention includes the step of adding to a basal medium simultaneously: FGF; at least one phospholipid; at least one fatty acid; and at least two factors selected from the group consisting of EGF, CTGF, VEGF, and ascorbic acid compound.

The culture method of the present invention may further include the step of adding to the basal medium at least one factor selected from the group consisting of TGF-β, HGF, and PDGF.

For a fuller understanding of the nature and advantages of the invention, reference should be made to the ensuing detailed description taken in conjunction with the accompanying drawings.

BRIEF DESCRIPTION OF DRAWINGS

FIG. 2 illustrates morphologic changes in human mesenchymal stem cells (MSC) cultured in serum-free culture media.

FIG. 3 illustrates evaluations of osteogenic differentiation potentials of human mesenchymal stem cells (MSC) cultured in serum-free culture media.

FIG. 4 illustrates evaluations of adipogenic differentiation potentials of human mesenchymal stem cells (MSC) cultured in serum-free culture media.

FIG. 6 illustrates evaluations of chondrogenic differentiation potentials of human mesenchymal stem cells (MSC) cultured in serum-free culture media.

FIG. 13 is a table illustrating a substance alternative to serum to be added in a serum-free culture medium for mesenchymal stem cells (MSC).

FIG. 14 is a table illustrating a substance alternative to serum to be added in a serum-free culture medium for C2C12 cells.

FIG. 15 (*b*) is a graph illustrating how addition of a substance alternative to serum in serum-free culture media affected proliferation of human mesenchymal stem cells (MSC).

FIG. 16 (*a*) is a graph illustrating how addition of a substance alternative to serum in serum-free culture media affected proliferation of primary human mesenchymal stem cells (MSC).

FIG. 16 (*b*) is a graph illustrating how addition of a substance alternative to serum in serum-free culture media affected proliferation of primary human mesenchymal stem cells (MSC).

FIG. 17 (b) is a graph illustrating how addition of a substance alternative to serum in serum-free culture media affected proliferation of CHO cells.

FIG. 17 (c) is a graph illustrating how addition of a substance alternative to serum in serum-free culture media affected proliferation of human skin-derived fibroblasts.

BEST MODE FOR CARRYING OUT THE INVENTION

Figure 1:
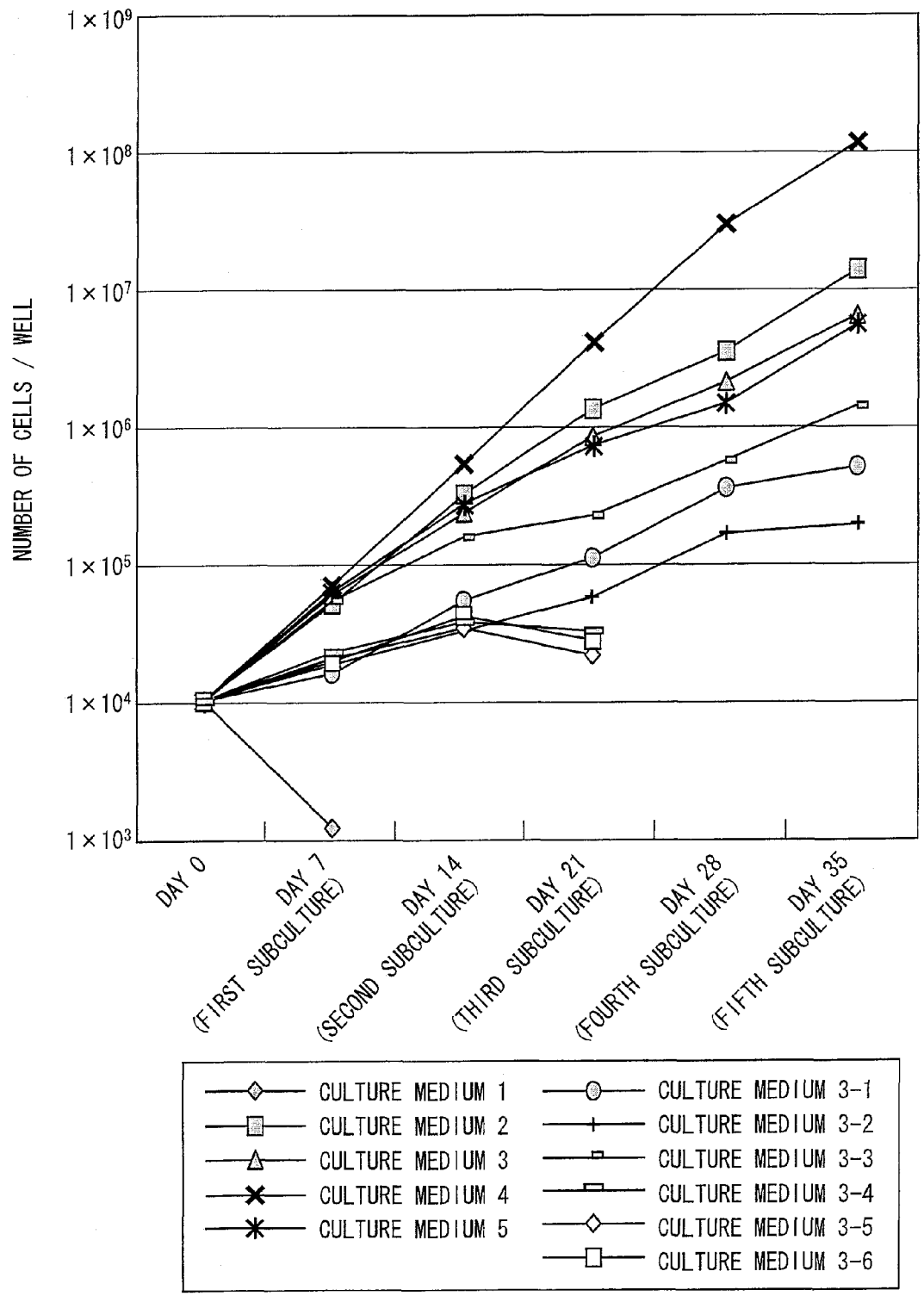
FIG. 1 is a graph illustrating how addition of a substance alternative to serum in serum-free culture media affected proliferation of human mesenchymal stem cells (MSC).

As described above, a variety of peptide hormones, growth factors, lipids are used in a culture medium containing no serum (a serum-free culture medium) so that cells are cultured without losing its proliferation property. However, a culture medium in which such components alternative to serum are added does not necessarily have a sufficient promoting effect on cell proliferation, compared with a culture medium containing serum. On this account, the inventors of the present invention studied a method of culturing a human mesenchymal stem cell, which is comparable, even under a low-serum (0.25 to 2%) condition, to a conventional culture method that uses a culture medium containing 10% serum. As a result, the inventors found that, when a specified growth factor group and a fatty acid complex are added to a basal medium, it is possible to obtain, even under a low-serum condition, cell proliferation equal to or greater than that obtained in culture by use of a culture medium containing 10% serum, thereby accomplishing a "base medium" for culturing a human mesenchymal stem cell. Moreover, studies on the conditions were further conducted, with the result that the inventors found a condition which allows, even under a serum-free condition, when a specified factor is further added, cell proliferation equal to or greater than that obtained in culture by use of a culture medium containing 10% serum.

With the use of the present invention, it is possible to proliferate an animal cell in large numbers in a culture system under a low-serum condition or serum-free condition. Especially, the present invention makes it possible to proliferate a cell like a mesenchymal stem cell having a regenerative medical purpose not only in a test tube but also in an industrial scale, and further to largely reduce its production cost.

(1) Culture Medium Additive for Use in Serum-Free Culturing of Animal Cells

The present invention provides a culture medium additive for use in serum-free culturing of animal cells. A culture medium additive of the present invention contains: at least three growth factors selected from the group constituted of FGF, PDGF, TGF-β, and HGF; and at least one phospholipid.

The phospholipid contained in the culture medium additive of the present invention encompasses, for example, phosphatidic acid, lysophosphatidic acid, phosphatidylinositol, phosphatidylserine, phosphatidylethanolamine, phosphatidyl choline, and phosphatidylglycerol. The culture medium additive may contain these phospholipids solely or in combination. In one embodiment, the culture medium additive of the present invention contains a combination of phosphatidic acid and phosphatidyl choline. These phospholipids may be derived from an animal or a plant.

In one embodiment, it is preferable that the culture medium additive contain at least one fatty acid. The fatty acid contained in the culture medium additive of the present embodiment encompasses, for example, linoleic acid, oleic acid, linolenic acid, arachidonic acid, myristic acid, palmitoyl acid, palmitic acid, and stearic acid. The culture medium additive of the present embodiment may contain these fatty acids solely or in combination. Moreover, the culture medium additive of the present embodiment may further contain cholesterol in addition to the fatty acid.

FGF used in the present description is intended to be a growth factor selected from a fibroblast growth factor (FGF) family, and is preferably FGF-2 (bFGF). Further, the FGF may be FGF-1 or the like selected from other families. PDGF used in the present description is intended to be a growth factor selected from a platelet derived growth factor (PDGF) family, and is preferably PDGF-BB or PDGF-AB. Moreover, TGF-β used in the present description is intended to be a growth factor selected from a transforming growth factor-β (TGF-β) family, and is preferably TGF-β. The TGF-β may be selected from other TGF-β families.

The culture medium additive of the present invention may further contain at least two factors selected from the group consisting of epidermal growth factor (EGF), connective tissue growth factor (CTGF), vascular endothelial growth factor (VEGF), and ascorbic acid compound.

Ascorbic acid compound used in the present description is intended to be an ascorbic acid (vitamin C) or an ascorbic acid 2-phosphate, or a compound similar thereto.

A growth factor contained in the culture medium additive of the present invention may be a natural product or a genetically modified product.

In one aspect, it is preferable that the culture medium additive of the present invention contain a lipid oxidation inhibitor. In one embodiment, a lipid oxidation inhibitor contained in the culture medium additive of the present invention can be DL-α-tocopherol acetate (vitamin E). The culture medium additive of the present invention may further include a surfactant. In one embodiment, a surfactant contained in the culture medium additive can be Pluronic F-68 or Tween-80.

The culture medium additive of the present invention may further contain insulin, transferrin and selenate. Insulin used in the present description may be an insulin-like growth factor and a product derived from a natural cell or genetically modified. The culture medium additive of the present invention may further contain dexamethasone or other glucocorticoid.

(2) Kit for Use in Serum-Free Culturing of Animal Cells

The present invention provides a culture medium additive kit for use in serum-free culturing of animal cells. A culture medium additive kit of the present invention includes: at least three growth factors selected from the group consisting of FGF, PDGF, TGF-β, and HGF; and at least one phospholipid. The culture medium additive kit of the present invention may include, in the same container, at least three growth factors selected from the group consisting of FGF, PDGF, TGF-β, and HGF; and at least one phospholipid, or may include these components separately.

In one embodiment, it is preferable that the culture medium additive kit of the present invention further include at least one fatty acid. The culture medium additive kit of the present invention may include, in the same container, at least three growth factors selected from the group consisting of FGF, PDGF, TGF-β, and HGF; at least one phospholipid; and at least one fatty acid, or may include these components separately.

In the present description, a "composition" means a form in which each main component is contained in one substance, and a "kit" means a form in which at least one of the main components is contained in different substance(s). On this account, it is easily understood that the growth factors, the phospholipid, and the fatty acid that are included in the culture medium additive kit of the present invention are the same as the ones described above in relation to the culture medium additive.

(3) Culture Medium for Use in Serum-Free Culturing Of Animal Cells

The present invention provides a culture medium for use in serum-free culturing of animal cells. A culture medium of the present invention contains: at least three growth factors selected from the group consisting of FGF, PDGF, TGF-β, and HGF; and at least one phospholipid. These components may be added to a basal medium at the same time or respectively. It follows that the culture medium of the present invention may contain components contained in the aforementioned culture medium additive, or components included in the aforementioned culture medium additive kit.

In one embodiment, it is preferable that the culture medium of the present invention contain at least one fatty acid. The culture medium of the present embodiment may include: at least three growth factors selected from the group consisting of FGF, PDGF, TGF-β, and HGF; at least one phospholipid; and at least one fatty acid. These components may be added to a basal medium at the same time or respectively. It follows that the culture medium of the present invention may contain components contained in the aforementioned culture medium additive, or components included in the aforementioned culture medium additive kit.

A basal medium for constituting the culture medium of the present invention is not especially limited, and may be a culture medium for an animal cell that is well known in the related field. A preferable basal medium encompasses, for example, Ham's F12 culture medium, DMEM culture medium, RPMI-1640 culture medium, and MCDB culture medium. These basal media may be used solely or in combination. In one embodiment, it is preferable that a basal medium for constituting the culture medium of the present invention be a culture medium in which MCDB and DMEM are mixed at a ratio of 1:1.

(4) Culture Method for Use in Serum-Free Culturing of Animal Cell

The present invention provides a culture method for serum-free culturing of an animal cell. A culture method of the present invention includes the step of culturing an animal cell in a culture medium that contains: at least three growth factors selected from the group consisting of FGF, PDGF, TGF-β, and HGF; and at least one phospholipid. The culture medium may further contain at least one fatty acid. It follows that the culture method of the present invention may use the aforementioned culture medium for culturing an animal cell.

In one embodiment, the culture method of the present invention may include the step of adding to a basal medium simultaneously; at least three growth factors selected from the group consisting of FGF, PDGF, TGF-β, and HGF; and at least one phospholipid. The basal medium is not especially limited, and may be a culture medium for an animal cell that is well known in the related field, as described above.

(5) Other Usage

As such, according to the present invention, it is possible that, even in a case where a serum-free culture medium is used, an animal cell is proliferated, while maintaining its properties, at a speed equal to or faster than a case where an animal cell is cultured in a culture medium containing 10% serum. If a stem cell (especially, a human mesenchymal stem cell) is cultured in accordance with the present invention, then it is possible to continuously subculture the stem cell while maintaining its properties (an osteogenic differentiation potential, an adipogenic differentiation potential, and the like) at a high level. As shown in examples, with the use of the serum-free culture medium of the present invention, it is possible to increase the number of cells at least 10000 times or more than that at the beginning of culture. On this account, the present invention also provides a culture medium additive, a culture medium additive kit, a culture medium, and a culture method, each of which is for continuously subculturing a stem cell.

In one aspect, the present invention provides a culture medium additive for continuously subculturing a stem cell. A culture medium additive of the present invention contains: at least three growth factors selected from the group consisting of FGF, PDGF, TGF-β, and HGF; and at least one phospholipid. In one embodiment, it is preferable that the culture medium additive of the present invention further contain at least one fatty acid.

In another aspect, the present invention provides a culture medium additive kit for continuously subculturing a stem cell. A culture medium additive kit of the present invention includes: at least three growth factors selected from the group consisting of FGF, PDGF, TGF-β, and HGF; and at least one phospholipid. In one embodiment, it is preferable that the culture medium additive of the present invention further include at least one fatty acid.

In another aspect, the present invention provides a culture medium for continuously subculturing a stem cell. A culture medium of the present invention contains: at least three growth factors selected from the group consisting of FGF, PDGF, TGF-β, and HGF; and at least one phospholipid. In one embodiment of the present invention, it is preferable that the culture medium of the present invention contain at least one fatty acid.

In further another aspect, the present invention provides a culture method for continuously subculturing a stem cell. A culture method of the present invention contains the step of culturing an animal cell in a culture medium which contains: at least three growth factors selected from the group consisting of FGF, PDGF, TGF-β, and HGF; and at least one phospholipid. The culture medium may further contain at least one fatty acid. It follows that the culture method of the present invention may use the aforementioned culture medium for continuously subculturing a stem cell.

As described in examples, the present invention has a greater effect on an undifferentiated cell such as a stem cell, and further has a great effect on serum-free culture of a cell (for example, a monkey kidney-derived COS cell) that is nearly in an undifferentiated state because a specified differentiation potential is lost. A cell to which the present invention can be applied is preferably an undifferentiated cell. The undifferentiated cell can be a stem cell such as a bone marrow-derived undifferentiated mesenchymal stem cell, a skeletal muscle stem cell, a hematopoietic stem cell, a neural stem cell, a hepatic stem cell, an adipose-derived stem cell, an adipose-derived progenitor cell, a vascular endothelial progenitor cell, a cartilage progenitor cell, a lymphoid progenitor cell, an NK progenitor cell, an embryo stem cell, or a fibroblast. The mesenchymal stem cell is more preferable. A culture method to be considered for culturing these cells may follow a well-known culture method for culturing each of the cells.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

All the academic documents and patent documents cited in the present description are incorporated in the present description.

EXAMPLES

Preparation of Components

Ten milligrams of 3-sn-phosphatidyl choline from egg yolk (PC, Wako: 163-21181) or 3-sn-phosphatidic acid from egg yolk (PA, Sigma: P9511) was added in 10 ml of PBS containing 0.01% of Tween-80 (−). A suspension of the liquid thus prepared was prepared by treating the liquid ultrasonically for five minutes. The suspension thus prepared was ultrasonically treated in ice for 30 seconds, and then centrifuged (2500 rpm) at ambient temperature for 5 minutes. In a case where precipitates were formed, the suspension was further ultrasonically treated on ice for 5 minutes. These processes were repeated until no precipitate was formed. The resultant solution was filtered with a filter of 0.45 μm in mesh size. The solution was sealed in with nitrogen gas, and refrigerated in dark. Each solution thus prepared was added to a culture medium by an amount of 1/100 of the culture medium. Chemically defined lipid concentrate (CD, Gibco: 11905-031), which is a fatty acid complex, was added to the culture medium by an amount of 1/100 of the culture medium. FIGS. 13 and 14 shows lipids contained in the fatty acid complex. FIG. 13 shows components in a culture medium used to culture a mesenchymal stem cell (MSC). FIG. 14 shows components in a culture medium used to culture a C2C12 cell. Each component may have a higher concentration than the upper limit of an optimum concentration shown in FIG. 13 or 14.

Three hundred nanograms per milliliter of FGF-2 was dissolved in a culture medium containing 1 mg/ml of BSA (Bovine Serum Albumin), so as to prepare a stock solution (1 in 100 solution). One thousand nanograms per milliliter of EGF was dissolved in a culture medium, so as to prepare a stock solution (1 in 100 solution). One thousand micrograms per milliliter of insulin was dissolved in a culture medium so as to prepare a stock solution (1 in 100 solution). These stock solutions were diluted 100 times for use. Dexamethasone was used in a final concentration of 10-8M.

Example 1

Serum Free Culturing of Marrow-Derived Mesenchymal Stem Cell: MSC

[I: Effect of Phospholipid]

Human ilium-marrow-derived mesenchymal stem cells (the third subculture: purchased from Bio-Whittaker Inc. (Walkersville, Md.)) were (i) washed three times with a DMEM culture medium that contained no serum, (ii) inoculated on a 24-well plate at a density of 5000 cells/cm$^2$, and (iii) cultured at 37° C. in a $CO_2$ incubator containing 5% $CO_2$.

The culturing was carried out with the following culture media whose basal medium was DMEM/MCDB=1:1, and to which the following additives were added.
(Culture medium 1) No additives
(Culture medium 2) 10% FBS (fetal bovine serum)
(Culture medium 3) Growth factors and fatty acids
(Culture medium 4) Growth factors, fatty acids, and phospholipids (PA, PC)

Components of fetal bovine serum (FBS) differ lot by lot. Therefore, a growth effect on cultured cells differs lot by lot. In the present example, in view of this, the culture medium 2 was prepared with FBS that especially exerted a high proliferation effect on mesenchymal stem cells.

Table 1 shows a composition of a basal medium of a serum-free culture medium. Components added to the basal medium were purchased from the companies shown in FIGS. 13 and 14. An MCDB201 culture medium (Sigma: M-6770), which is a basal medium, was developed for clonal proliferation of a chicken embryo fibroblast. The MCDB201 culture medium contains a complete trace element. In contrast with DMEM or DMEM/Ham's F-12, which are conventional basal media for culturing mesenchymal stem cells, employment of MCDB201/DMEM (1:1) resulted in an optimal promoting effect on the proliferation of the mesenchymal stem cells (not shown in figures).

TABLE 1

| Composition | DMEM/F-12 (g/L) | MCDB201/DMEM (g/L) |
|---|---|---|
| AMINO ACIDS | | |
| L-Alanine | 0.00445 | 0.00445 |
| L-Arginine•HCl | 0.1474 | 0.0736 |
| L-Asparagine•$H_2O$ | 0.0075 | 0.0075 |
| L-Aspartic Acid | 0.00665 | 0.00665 |
| L-Cystine•HCl•$H_2O$ | 0.03129 | 0.01756 |
| L-Cysteine•2HCl | 0.01756 | 0.0313 |
| L-Glutamic Acid | 0.00735 | 0.00735 |
| L-Glutamine | 0.365 | 0.292 |
| Glycine | 0.01875 | 0.01875 |
| L-Histidine•HCl•$H_2O$ | 0.0314 | 0.0314 |
| L-Isoleucine | 0.05447 | 0.05906 |
| L-Leucine | 0.05905 | 0.07217 |
| L-Lysine•HCl | 0.09125 | 0.09125 |
| L-Methionine | 0.01724 | 0.01724 |
| L-Phenylalanine | 0.03548 | 0.03548 |
| L-Proline | 0.01725 | 0.00288 |
| L-Serine | 0.02625 | 0.03676 |
| L-Threonine | 0.05345 | 0.06537 |
| L-Tryptophan | 0.00902 | 0.01106 |
| L-Tyrosine•2Na•2$H_2O$ | 0.05579 | 0.05757 |
| L-Valine | 0.05285 | 0.06456 |
| VITAMINS | | |
| D-Biotin | 0.0000035 | 0.0000035 |
| Choline Chloride | 0.00898 | 0.00898 |
| Folic Acid | 0.00266 | 0.00266 |
| Folinic Acid•Ca | — | 0.00000256 |
| myo-Inositol | 0.0126 | 0.0126 |
| Niacinamide | 0.00202 | 0.00505 |
| D-Pantothenic Acid•½Ca | 0.00224 | 0.00224 |
| Pyridoxal•HCl | 0.0020506 | — |
| Pyridoxine•HCl | — | 0.0020308 |
| Riboflavin | 0.000219 | 0.0002565 |
| DL-Thioctic Acid | 0.000105 | 0.000105 |
| Thiamine•HCl | 0.00219 | 0.00219 |
| Vitamin B-12 | 0.00068 | 0.00068 |
| MAGOR INORGANIC SALTS | | |
| $CaCl_2$•2$H_2O$ | 0.1545 | 0.2795 |
| KCl | 0.3118 | 0.3118 |
| $MgSO_4$ | 0.04884 | 0.13912 |
| NaCl | 6.996 | 6.996 |
| $NaHCO_3$ | 1.2 | 1.85 |
| $Na_2HPO_4$(anhyd) | 0.07102 | 0.0355 |
| $NaH_2PO_4$ | 0.0543 | 0.0543 |
| TRACE ELEMENTS | | |
| $CuSO_4$•5$H_2O$ | 0.0000013 | 0.00000025 |
| $FeSO_4$•7$H_2O$ | 0.000417 | 0.000834 |
| $Fe(NO_3)_3$•9$H_2O$ | 0.00005 | 0.00005 |
| $Na_2SeO_3$ | — | 0.0000004325 |
| $NaSiO_3$•9$H_2O$ | — | 0.000071 |
| $(NH_4)_2MO_4$•4$H_2O$ | — | 0.000000309 |
| $NH_4VO_3$ | — | 0.000000003 |
| $NiCl_2$•6$H_2O$ | — | 0.0000000006 |
| $MgCl$•6$H_2O$ | 0.0612 | — |
| $MnSO_4$ | — | 0.000000375 |
| $ZnSO_4$•7$H_2O$ | 0.000432 | 0.00001437 |

TABLE 1-continued

| Composition | DMEM/F-12 (g/L) | MCDB201/DMEM (g/L) |
| --- | --- | --- |
| OTHER ORGANIC COMPOUNDS | | |
| Adenine | — | 0.00086 |
| D-Glucose | 3.15 | 1.2205 |
| HEPES | — | 3.5745 |
| Hypoxanthine | 0.0021 | — |
| Linoleic Acid | 0.000042 | 0.000042 |
| Phenol Red•Na | 0.00863 | 0.00863 |
| Putrescine•HCl | 0.000081 | 0.0000000805 |
| Pyruvic Acid•Na | 0.055 | 0.0275 |
| Thymidine | 0.000365 | 0.00003635 |

A base medium of the present invention (culture medium 3) contained growth factors (FGF, HGF, TGF-β, and PDGF) and a fatty acid complex (arachidonic acid, retinoic acid, linolenic acid, oleic acid, linolenic acid, myristic acid, palmitoyl acid, palmitic acid, and stearic acid). In addition, the base medium contains insulin, transferrin, selenate (sodium selenate etc.), cholesterol, dexamethasone (Dex), and bovine serum albumin (BSA), which are knows as medium supplements. Furthermore, the base medium contained vitamin E as a lipid oxidation inhibitor, Pluronic F-68 and Tween-80 as surfactants.

The experiments were conducted with three samples per culture medium (n=3). The culture media were replaced every 2 to 3 days. The mesenchymal stem cells were washed two times with PBS before becoming confluent, and were then incubated for two minutes in PBS containing 0.05% trypsin and 0.2 mM EDTA, so that the mesenchymal stem cells were detached from the plate. Then, the mesenchymal stem cells were re-suspended with a plant-derived trypsin inhibitor (Sigma: T6522) that did not contain serum. After the mesenchymal stem cells were washed three times with a DMEM culture medium that did not contain serum, the number of cells was counted by use of a Coulter counter (Z1 single, Coulter Inc.). FIG. 1 shows results.

For the sake of subculturing of mesenchymal stem cells, with the use of each of the culture media, re-suspended mesenchymal stem cells were re-inoculated on a 24-well plate at a density of 5000 cells/cm². Subculturing was repeated every 7 days until the fifth subculture. FIG. 1 shows averages±SD, as a result of the experiments conducted with three samples per culture medium (n=3).

Addition of 2% FBS gave the base medium of the present invention (the culture medium 3) a cell proliferation effect equal to that of the conventional culture medium containing 10% FBS (not shown in figures). With the use of the base medium under a serum-free condition, a fine cell proliferation effect was obtained although the effect fell short of that of the culture medium containing 10% FBS. That is, the effect was approximately 45% of that of the culture medium containing 10% FBS (see FIG. 1). Animal-derived phospholipids (phosphatidic acid (PA) and phosphatidylcolin (PC)) were added to the base medium (the culture medium 3), thereby the culture medium 4 being prepared. With the use of the culture medium 4, a fine cell proliferation effect was obtained even under a serum-free condition. That is, the effect was approximately 8.5 times that of the culture medium containing 10% FBS (see FIG. 1).

The experiments demonstrated that serum-free culture of a human mesenchymal stem cell could be significantly improved by adding phospholipids to a serum-free culture medium containing growth factors and fatty acids.

[II. Effect of Fatty Acids]

Further study was conducted on the importance of fatty acids in the base medium.
(Culture medium 1) No additives
(Culture medium 2) 10% FBS (fetal bovine serum)
(Culture medium 3) Growth factors and fatty acids
(Culture medium 5) Growth factors+linolenic acid+lecithin+EGF+vitamin C (VC)

The culture medium 5 was a medium which was similar to the base medium (the culture medium 3) except that fatty acids except linolenic acid were not added and plant-derived phospholipid (lecithin) was added thereto. The plant-derived phospholipid (lecithin) was prepared by the following method.

Two hundred milligrams of plant-derived lecithin (Lecithin from Soybean, Wako: 120-00832) was added to chloroform. The resultant was dried by nitrogen gas distillation and 20 ml of PBS was added to the dried resultant. The solution thus prepared was ultrasonically treated at ambient temperature for 15 minutes so that the solution was equilibrated. In nitrogen gas, the solution was further ultrasonically treated on ice for a period of time in a range of 30 seconds to 2 minutes. The solution was centrifuged at ambient temperature for 5 minutes (2500 rpm). When precipitates were formed, the solution was further ultrasonically treated on ice for 5 minutes, and then centrifuged at ambient temperature for 5 minutes (2500 rpm). After these processes were repeated, a supernatant liquid was collected. The supernatant liquid was filtered with a filter of 0.45 μm in mesh size. The supernatant liquid was sealed in with nitrogen gas and refrigerated in dark.

As illustrated in FIG. 1, with the use of the culture medium 5, a fine cell proliferation effect was obtained even under a serum-free condition. The effect was equivalent to that of the base medium (the culture medium 3) and was approximately 40% of that of the culture medium containing 10% FBS (see FIG. 1).

As the experiments demonstrated, if a serum-free culture medium containing growth factors further contained at least one fatty acid, then it was possible to obtain an effect of phospholipid on a cell proliferation in serum-free culture of a human mesenchymal stem cell.

[III: Effect of Growth Factors]

Further study was conducted on the growth factors to be added to a culture medium by comparing results of serum-free proliferation of mesenchymal stem cells with the use of culture media that were similar to the base medium (culture medium 3) except that certain one of the growth factors was not added therein.
(Culture medium 1) No additives
(Culture medium 3) Growth factors and fatty acids
(Culture medium 3-1) Only PDGF was lacked from the culture medium 3.
(Culture medium 3-2) Only TGF-β was lacked from the culture medium 3.
(Culture medium 3-3) Only HGF was lacked from the culture medium 3.
(Culture medium 3-4) Only FGF was lacked from the culture medium 3.
(Culture medium 3-5) Only dexamethasone (Dex) was lacked from the culture medium 3.
(Culture medium 3-6) Insulin, transferrin, and selenate were lacked from the culture medium 3.

As illustrated in FIG. 1, it was demonstrated that the lack of any one of the growth factors inhibited active proliferation of the mesenchymal stem cell under a serum-free condition. For example, the lack of only either of HGF or TGF-β obviously decreased the proliferation in the present culture. Furthermore, the lack of both of the HGF and the TGF-β significantly inhibited the cell proliferation (Result data is not shown here).

Figure 10:
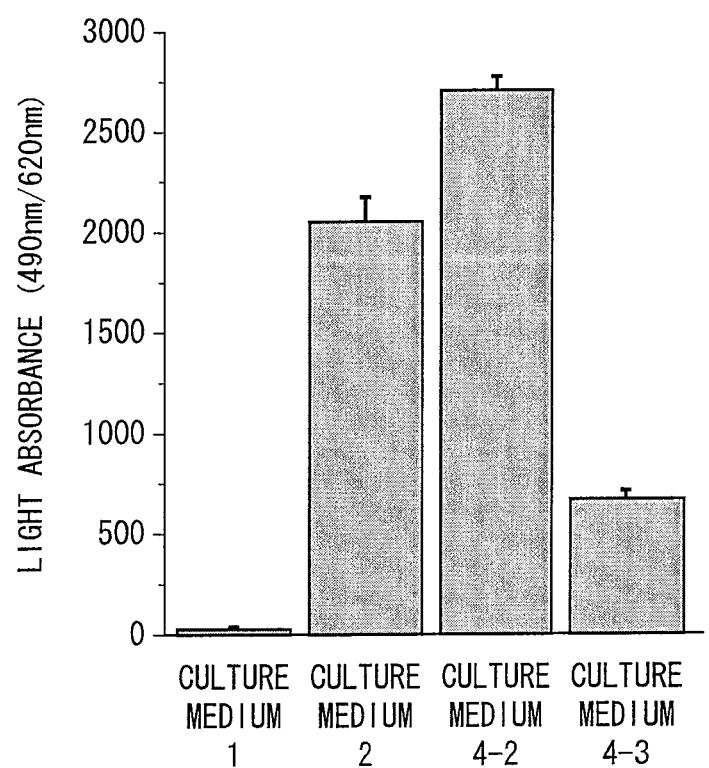
FIG. 10 is a graph illustrating how addition of a substance alternative to serum in serum free culture media affected on proliferation of C2C12 cells.

It was demonstrated that the use of a culture medium to which EGF and VC were added in addition to phospholipids (culture medium 4+EGF+VC) could further promote the proliferation of a mesenchymal stem cell in a serum-free culture medium although this is not shown in FIG. 1 (see FIG. 10: culture medium 4-2).

[IV: Influence on Morphology of Mesenchymal Stem Cell]

FIG. 2 shows morphology of the mesenchymal stem cells cultured in the serum-free culture media of the present example. As FIG. 2 shows, cells cultured in the serum-free media (the third subculture) had a spindle shape, which is typical of mesenchymal stem cells, in comparison with cells cultured in the culture medium containing 10% FBS. The use of a serum-free culture medium from which only either of TGF-β or HGF was lacked caused a decrease in cell proliferation.

Example 2

Evaluation of Differentiation Potential of Mesenchymal Stem Cells Cultured Under Serum-Free Condition

[I: Differentiation Induction to Osteoblast Cells]

For the sake of evaluation of differentiation potentials of the mesenchymal stem cells that had been proliferated with the use of the serum-free media of Example 1, the third subculture of human ilium-derived mesenchymal stem cells that had been obtained through continuous subculturing with the use of serum-free culture media were collected and moved to osteogenic-differentiation-inductive culture media containing α-MEM, 10% FBS, 100 nM of dexamethasone, 10 mM of β-glycerophosphoric acid, and 50 μg/ml of L-ascorbic acid 2-phosphate. The mesenchymal stem cells in the osteogenic-differentiation-inductive culture media were cultured at 37° C. in 5% carbon dioxide gas for 28 days in total. The media was replaced every 2 to 3 days with media having the same content. A cell layer differentiated to bone and then calcified was stained with alizarin crimson. FIG. 3 shows results.

The mesenchymal stem cells cultured in the serum-free culture media (the fourth subculture) were cultured in the osteogenic-differentiation-inductive culture media for 28 days. As a result, as FIG. 3 shows, the mesenchymal stem cells showed alizarin crimson stainability, which indicates calcification peculiar to an osteoblast cell. Thus, deposition of calcium was observed. Furthermore, each of the mesenchymal stem cells cultured in the serum-free culture media had a high osteogenic differentiation potential (calcification potential), in comparison with the mesenchymal stem cells cultured in the culture medium containing 10% FBS. Especially, it was observed that the media to which two kinds of phospholipids had been added caused the mesenchymal stem cells to have the highest osteogenic differentiation potential.

[II: Differentiation Induction to Adipose Cells]

For the sake of evaluation of differentiation potentials of the mesenchymal stem cells that had been proliferated with the use of the serum-free media of Example 1, the third subculture of human ilium-derived mesenchymal stem cells that had been obtained through continuous subculturing with the serum-free culture media were proliferated until the cells became confluent. The cells were dispersed with trypsin and collected. Then, the cells were moved to adipogenic-differentiation-inductive culture media containing high-glucose DMEM, 10 μg/ml of insulin, 0.2 mM of indomethacin, 1 μM of dexamethasone, 0.5 mM of 3-isobutyl-1-methylxanthine, and 10% FBS. The mesenchymal stem cells in the adipogenic-differentiation-inductive culture media were cultured at 37° C. in 5% carbon dioxide gas for 28 days in total. The media were replaced every 2 to 3 days with media of the same content. The mesenchymal stem cells were stained with Oil Red O for the evaluation of adipogenic differentiation. FIG. 4 shows results.

The mesenchymal stem cells cultured in the serum-free culture media (the fourth subculture) were cultured in the adipogenic-differentiation-inductive culture media for 28 days. As a result, as FIG. 4 shows, the mesenchymal stem cells showed stainability with Oil Red O. This stainability indicates fat. Furthermore, each of the mesenchymal stem cells cultured in the serum-free culture media had a high adipogenic-differentiation potential, in comparison with the mesenchymal stem cells cultured in the culture medium containing 10% FBS.

[III: Differentiation Induction to Chondrocytes]

Figure 5:
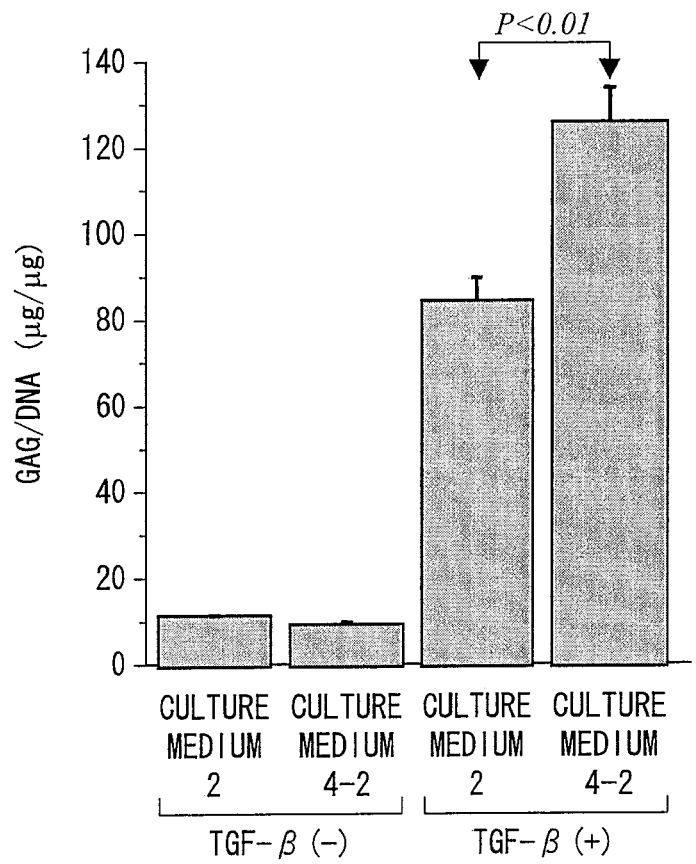
FIG. 5 is a graph illustrating evaluations of chondrogenic differentiation potentials of human mesenchymal stem cells (MSC) cultured in serum-free culture media.

For the sake of evaluation of differentiation potential of the mesenchymal stem cells that had been proliferated with the use of the serum-free medium of Example 1, the fifth subculture of human ilium-derived mesenchymal stem cells that had been obtained through continuous subculturing with the serum-free culture medium were collected and moved to a chondrocyte-differentiation-inductive culture medium. The chondrocyte-differentiation-inductive culture medium contained high-glucose α-MEM, 10 ng/ml of TGF-$β_3$, 100 nM of dexamethasone, 50 μg/ml of L-ascorbic acid 2-phosphate, 100 μg/ml of sodium pyruvate, and ITS plus (6.25 μg/ml of transferrin, 6.25 μg/ml of insulin, 6.25 ng/ml of selenate, 5.33 μg/ml of linoleic acid, and 1.25 mg/ml of bovine serum albumin: BSA). Two hundred thousand mesenchymal stem cells were put in a 15 ml centrifuging tube. The cells were incubated in the following 0.5 to 1 ml of a culture medium. Meanwhile, some mesenchymal stem cells were moved to a control culture medium in which TGF-β is lacked from the chondrocyte-differentiation-inductive culture medium. The mesenchymal stem cells in the chondrocyte-differentiation-inductive culture medium and those in the control culture medium were cultured at 37° C. in 5% carbon dioxide gas. After 24 hours from the initiation of culture, the cells formed global pellets. The cells were cultured for 21 days. The media were replaced every 2 or 3 days with media having the same content. A quantity of GAG in the pellets formed after the cells were cultured was determined with the use of a sulfated glycosaminoglycan (GAG) assay kit (Biocolor, Ltd.). FIG. 5 shows results. The quantity of GAG was normalized according to DNA content of the cells. After the culture, the cells that underwent chondrogenic-differentiation in the chondrocyte-differentiation-inductive culture medium were stained with toluidine blue. FIG. 6 shows results.

The mesenchymal stem cells cultured in the serum-free culture medium and those cultured in the culture medium containing 10% FBS were cultured in the chondrocyte-differentiation-inductive culture media for 21 days. As a result, as FIG. 5 shows, the mesenchymal stem cells cultured in the serum-free culture medium (the fifth subculture) contained a significantly high quantity of GAG (p<0.01) in comparison with that of the mesenchymal stem cells cultured in the culture medium containing 10% FBS. On the other hand, the mesenchymal stem cells cultured in the serum-free culture medium and those cultured in the culture medium containing 10% FBS were cultured respectively in control culture media for 21 days. As a result, an increase in the quantity of GAG was not observed in either of the control media (numeric values indicate averages±SD, as a result of the experiments conducted with three samples).

The mesenchymal stem cells cultured in the serum-free culture medium and those cultured in the culture medium containing 10% FBS were cultured in the chondrocyte-differentiation-inductive culture media for 21 days. As a result, as FIG. 6 shows, the mesenchymal stem cells cultured in the serum-free culture medium (the fifth subculture) showed a significantly high stainability with toluidine blue in comparison with the mesenchymal stem cells cultured in the culture medium containing 10% FBS. Thus, accumulation of a matrix was observed.

Example 3

Effect of Growth Factors on Serum-Free Culturing of Marrow-Derived Mesenchymal Stem Cell Human ilium-marrow-derived mesenchymal stem cells (the third subculture) were (i) washed three times with a DMEM culture medium that does not contain serum, (ii) inoculated on a 24-well plate at a density of 5000 cells/cm$^2$, and (iii) cultured at 37° C. in a $CO_2$ incubator with 5% $CO_2$.

Figure 7:
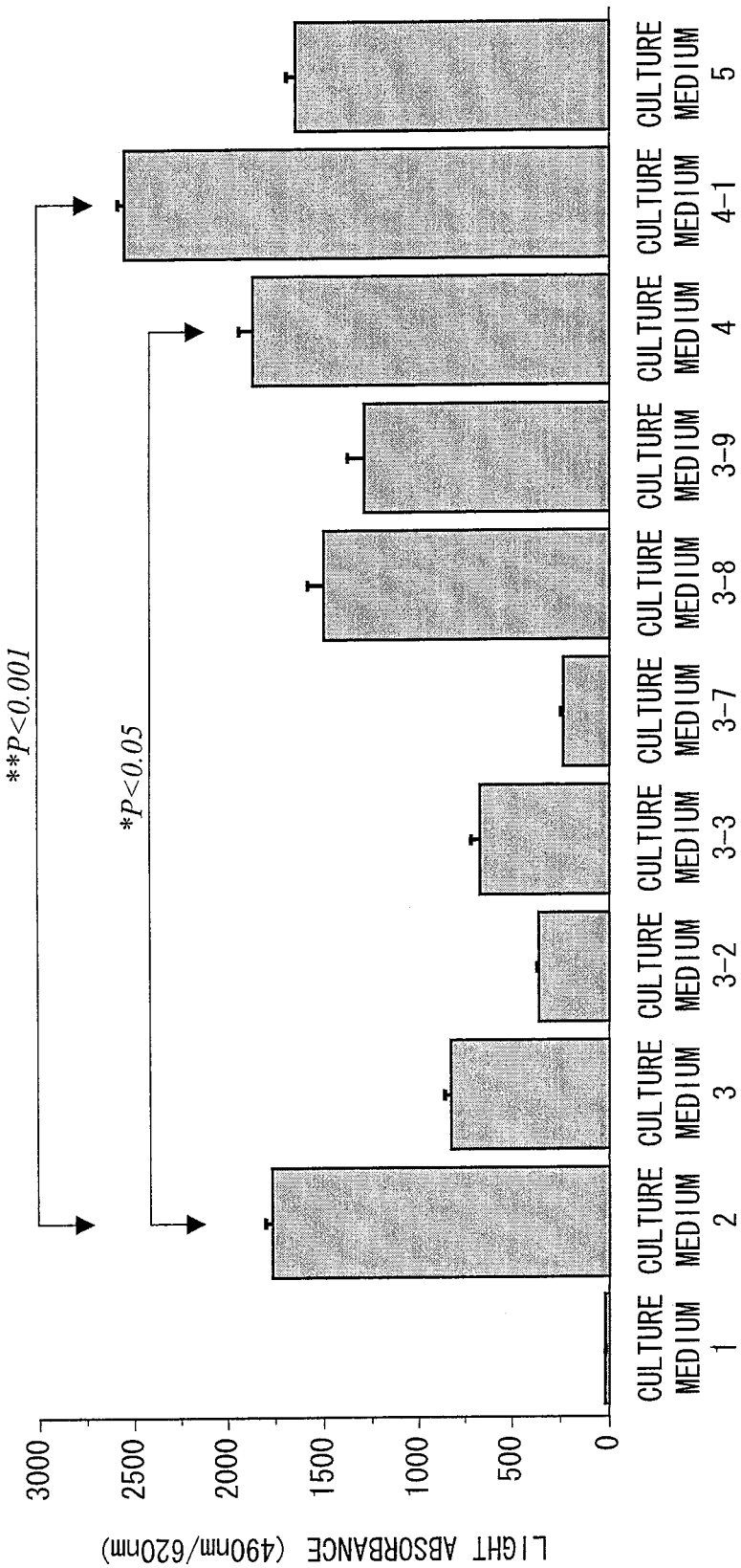
FIG. 7 is a graph illustrating how addition of a substance alternative to serum in serum-free culture media affected proliferation of human mesenchymal stem cells (MSC).

The culturing was carried out with the following culture media whose basal medium was DMEM/MCDB=1:1, and to which the following additives were added.
(Culture medium 1) No additives
(Culture medium 2) 10% FBS (fetal bovine serum)
(Culture medium 3) Growth factors and fatty acids
(Culture medium 3-2) Only TGF-β was lacked from the culture medium 3.
(Culture medium 3-3) Only HGF was lacked from the culture medium 3.
(Culture medium 3-7) TGF-β and HGF were lacked from the culture medium 3.
(Culture medium 3-8) Culture medium 3+EGF
(Culture medium 3-9) Culture medium 3+VC
(Culture medium 4) Growth factors, fatty acids, and phospholipids (PA, PC)
(Culture medium 4-1) Culture medium 4+EGF+vitamin C (VC)+vitamin E (VE)
(Culture medium 5) Growth factors+linolenic acid+lecithin+EGF+VC The experiments were conducted with three samples per culture medium (n=3). The media were replaced every 2 or 3 days. The number of cells of the eighth day of the culture was counted by use of a cell counting kit WST-8 (Dojindo Lab.). FIG. 7 shows results.

As FIG. 7 shows, the mesenchymal stem cells cultured in serum-free culture media (the culture media 3-8, 4, 4-1, or 5) showed a high cell proliferation on the eighth day of the culture in comparison with the mesenchymal stem cells cultured in the culture medium 3 (numeric values indicate averages±SD, as a result of the experiments conducted with three samples). Especially, this effect was significant in the cells cultured in the culture media 4 and 4-1. The results demonstrated that the proliferation of the mesenchymal stem cells was effectively promoted not only by phospholipids, but also by EGF, VC, and a high concentration of VE. In contrast, the lack of at least one of TGF-β and HGF from the base medium (the culture medium 3) significantly decreased the proliferation of the mesenchymal stem cells. This demonstrated that TGF-β and HGF were essential to the serum-free culture of the mesenchymal stem cells.

The results also demonstrated that the serum-free culture of the mesenchymal stem cells was effectively promoted with the use of a medium containing a lipid mixture that contains plant-derived lecithin (corresponding to an animal-derived phosphatidylcolin (PC)) as its main component (i.e., the culture medium 5), as in the case of a culture medium containing a lipid mixture that contains many fatty acids as its main components (i.e., the culture medium 4) (see FIG. 7).

Example 4

Effect of Additional Growth Factors in Serum-Free Culturing of Human-Marrow-Derived Mesenchymal Stem Cell Human ilium-marrow-derived mesenchymal stem cells (the third subculture) were (i) washed three times with a DMEM culture medium that did not contain serum, (ii) inoculated on a 24-well plate at a density of 5000 cells/cm$^2$, and (iii) cultured at 37° C. in a $CO_2$ incubator with 5% $CO_2$.

Figure 8:
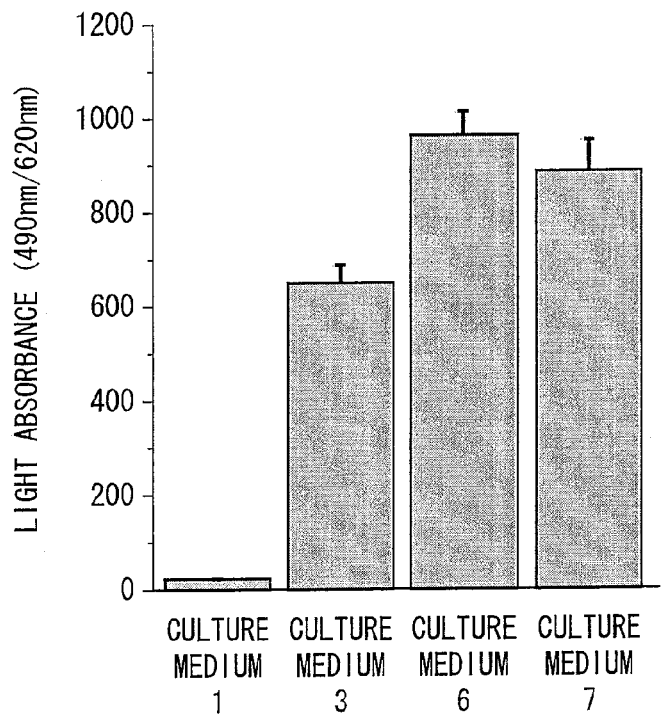
FIG. 8 is a graph illustrating how addition of a substance alternative to serum in a serum-free culture media affected proliferation of human mesenchymal stem cells (MSC).

The culturing was carried out with the following culture media whose basal medium was DMEM/MCDB=1:1, and to which the following additives were added.
(Culture medium 1) No additives
(Culture medium 3) Growth factors and fatty acids
(Culture medium 6) Culture medium 3+VEGF
(Culture medium 7) Culture medium 3+CTGF The experiments were conducted with three samples per culture medium (n=3). The media were replaced every 2 or 3 days. The number of cells of the eighth day of the culture was counted by use of a cell counting kit WST-8 (Dojindo Lab.). FIG. 8 shows results.

As FIG. 8 shows, the mesenchymal stem cells cultured in a serum-free culture medium (the culture medium 6 or 7) showed a high cell proliferation on the eighth day of the culture in comparison with the mesenchymal stem cells cultured in the culture medium 3 (numeric values indicate averages±SD, as a result of the experiments conducted with three samples).

Example 5

Serum-Free Culture of Marrow-Derived Mesenchymal Stem Cell

Human ilium-marrow-derived mesenchymal stem cells (the third subculture) were (i) washed three times with a DMEM culture medium that does not contain serum, (ii) inoculated on a 24-well plate at a density of 5000 cells/cm$^2$, and (iii) cultured at 37° C. in a $CO_2$ incubator with 5% $CO_2$.

Figure 9:
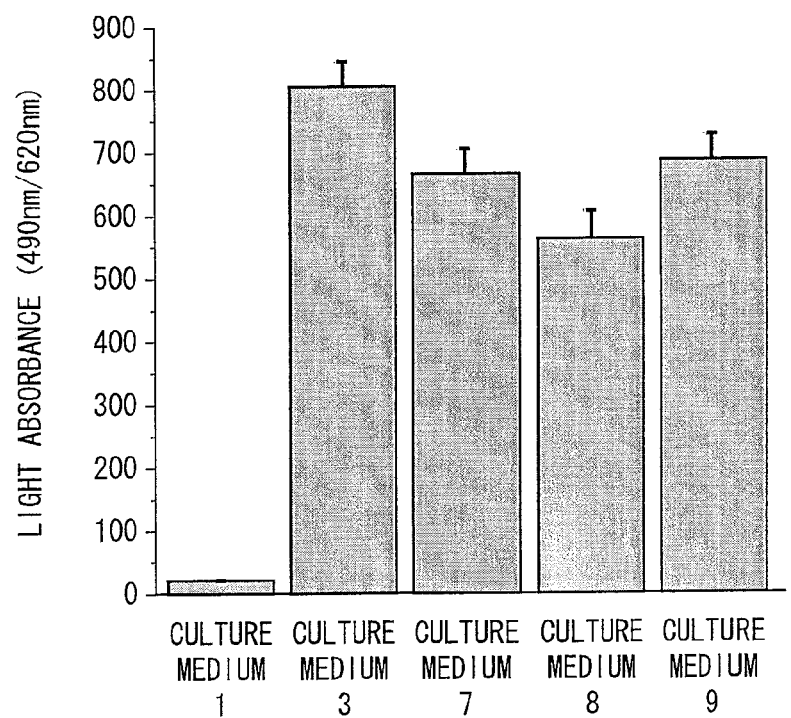
FIG. 9 is a graph illustrating how addition of a substance alternative to serum in serum-free culture media affected proliferation of human mesenchymal stem cells (MSC).

The culturing was carried out with the following culture media whose basal medium was DMEM/MCDB=1:1, and to which the following additives were added.
(Culture medium 1) No additives
(Culture medium 3) Growth factors and fatty acids
(Culture medium 7) Growth factors+linolenic acid+PC
(Culture medium 8) Growth factors+linolenic acid+PA
(Culture medium 9) Growth factors+linolenic acid+lecithin The experiments were conducted with three samples per culture medium (n=3). The media were replaced every 2 or 3 days. The number of cells of the eighth day of the culture was counted by use of a cell counting kit WST-8 (Dojindo Lab.). FIG. 9 shows results.

As FIG. 9 shows, the mesenchymal stem cells cultured in a serum-free culture medium (the culture medium 7 or 8) showed cell proliferation equivalent to proliferation of cells cultured in the culture medium 3 (numeric values indicate averages±SD, as a result of the experiments conducted with three samples). The mesenchymal stem cells cultured in a culture medium containing (i) a lipid mixture that contains lecithin as its main component which lecithin is a plant-derived phospholipid and (ii) retinoic acid (i.e., the culture medium 9) also showed cell proliferation equivalent to the proliferation of cells cultured in the base medium (the culture medium 3). That is, in a case where the growth factors that characterize the present invention were contained in a culture medium, even when a combination of the growth factors was one kind of fatty acid and one kind of phospholipid, mesenchymal stem cells could be proliferated although a growth rate thereof was low. The results demonstrated that a combination of more lipids made it possible to carry out mass culture faster than (i) a combination of one kind of fatty acid and one kind of phospholipid, (ii) a lipid mixture containing many fatty acids as its main component, or (iii) a lipid mixture containing as its main component lecithin that is a plant-derived phospholipid (compare FIG. 1 with FIG. 9).

Example 6

Serum-Free Culture of Undifferentiated Cell Line

Mouse mesenchymal stem cell C2C12 cells (or mouse chondrogenic cell lines ATDC5, or monkey kidney-derived undifferentiated cell line COS7 cells) were cultured in a $CO_2$ incubator with 5% $CO_2$ at 37° C. on a 10 cm-plate including a DMEM culture medium containing 10% fatal bovine serum, 100 unit/ml of penicillin, and 100 µg/ml of streptomycin. The cells were washed twice with PBS, and were then incubated for 2 minutes in PBS containing 0.05% trypsin and 0.2 mM EDTA, so that the cells were detached from the plate. Then, the cells were re-suspended with a plant-derived trypsin inhibitor (Sigma T6522) that contains no serum. After being washed three times with a DMEM culture medium containing no serum, the cells were counted by use of a Coulter counter (Z1 Single, Coulter co.). The results are shown in FIG. 10.

Further, the re-suspended cells were re-inoculated on a 24-well plate at a density of 5000/cm$^2$ with the use of the following different culture media.
(Culture medium 1) No additives
(Culture medium 2) 10% FBS
(Culture medium 4-2) Growth factors, fatty acids and phospholipids (PA, PC)+EGF+VC
(Culture medium 4-3) Growth factors, fatty acids and phospholipids (PA, PC)+EGF+VC−HGF The experiments were conducted with three samples per culture medium (n=3). The culture media were replaced every 2 or 3 days. On the eighth day in the culture, the cells were counted by use of a cell counting kit WST-8 (Dojindo Lab.). The results are shown in FIG. 10.

As shown in FIG. 10, the cell line C2C12 cells cultured in a serum-free culture medium (the culture medium 4-2) had further greater cell proliferation than that of cells cultured in a general culture medium containing 10% FBS (the culture medium 2). However, with the use of a culture medium (the culture medium 4-3) that lacked the HGF from the culture medium 4-2, a proliferation potential of the cell line remarkably decreased (numeric values indicate averages±SD, as a result of the experiments conducted with three samples per culture medium).

In a case of a mouse cell line ATDC5 that had been already differentiated into a cartilage from a mesenchymal stem cell, even when the serum-free culture medium (the culture medium 4-2) was used, it was difficult to obtain a promoting effect on cell proliferation comparable to a promoting effect obtained by culturing in the culture medium containing 10% FBS (the culture medium 2). That is to say, it was demonstrated that the serum-free culture medium (the culture medium 5) had a greater effect especially on an undifferentiated cell. Moreover, the serum-free culture medium of the present invention was also effective for serum-free culturing of cells that were nearly in an undifferentiated state because of losing a particular differentiation potential (for example, a monkey kidney-derived COST cell). In this case, the promoting effect on cell proliferation comparable to the promoting effect obtained by the culture in the culture medium containing 10% FBS (the culture medium 2) was obtained.

Example 7

Mechanism of Cell Proliferation in Serum-Free Culture Medium

For the purpose of clarifying a mechanism of cell proliferation in a serum-free culture medium, study was further conducted on activation of a mitogenic signal transduction system caused by each additive factor added into a serum-free culture medium. An active state of the mitogenic signal transduction system caused by each additive factor was analyzed by a western blot method. Here, in protein phosphoenzymes that are particularly closely related to cell proliferation, an extracellular signal control kinase Erk 1/2 and an Akt (a protein phosphoenzyme located downstream to PI3K, and related to regulations of cell functions) were focused in the present example. When the Erk1 1/2 and the Akt are phosphorylated, they are converted into active forms. In a culture medium containing 10% FBS on a 12-well plate, human mesenchymal stem cells (three cell lines) were cultured until the cells were in a subconfluent state. The cultured cells were washed twice with PBS, and were then further cultured for 16 hours in a serum-free culture medium containing 1.25 mg/ml of BSA (bovine serum albumin). After that, the cultured cells were incubated for minutes respectively: (i) in stimulating solutions respectively containing growth factors (E: EGF, F: FGF, G: PDGF, H: HGF, I: insulin, J: TGF-β), dexamethasone (D), transferrin (T); (ii) in stimulating solutions respectively containing fatty acid factors (A1: arachidonic acid, A2: linoleic acid, A3: linolenic acid, A4: oleic acid, A5: B1, A6: phosphatidic acid, A7: phosphatidyl choline); and (iii) in a controlling solution containing none of them. Further, each of the stimulating solutions, and the controlling solution were removed by suction on ice, and then, the cells were washed twice with PBS. The cells thus washed were dissolved in lysis buffer. The resultant cell lysis solution was centrifuged by 6.500 g for 10 minutes, and its supernatant liquid was electrophoresed on 10% SDS-polyacrylamide gel. Proteins thus separated into fractions were transferred on a PVDF membrane (made by Millipore Co.), and then, the fractions were analyzed with antiphosphorylation-specific Erk 1/2 antibody, or antiphosphorylation-specific Akt antibody (both are made by Cell Signaling technology Inc.). The results are shown in FIGS. 11 and 12.

Figure 11:
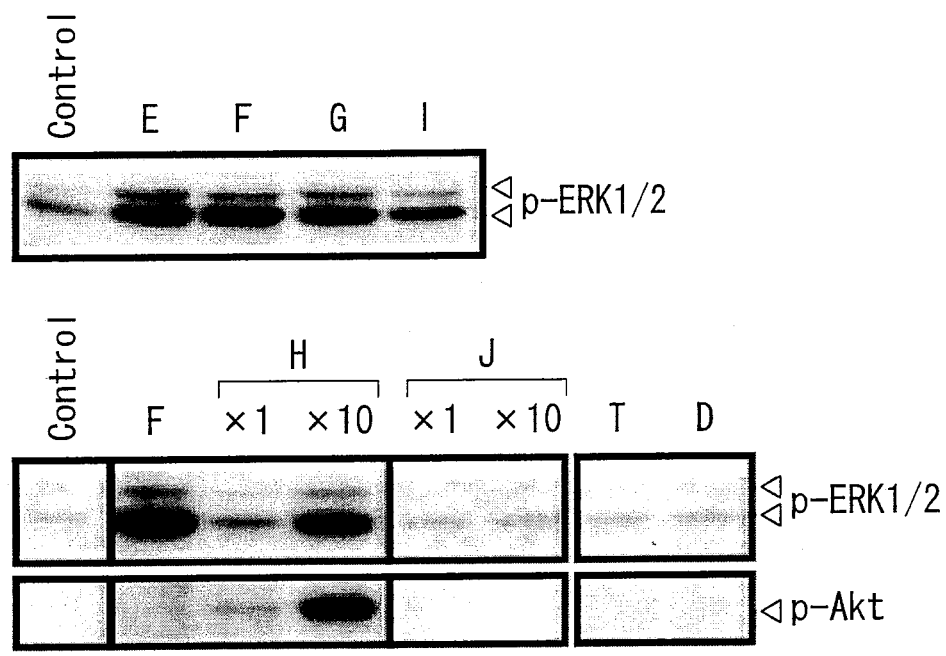
FIG. 11 illustrates how addition of a substance alternative to serum in serum-free culture media affected mitogenic signal transduction system of human mesenchymal stem cells (MSC).

FIG. 11 shows fractions of the proteins obtained from the cells stimulated by the growth factors (E through J), dexamethasone (D), and transferrin (T). As shown in FIG. 11, it was demonstrated that, compared with the controlled cells (which was not stimulated), the Erk 1/2 was more phosphorylated in the cells stimulated by the EGF (E), the FGF (F), the PDGF (G), insulin (I), and the HGF (H). Especially, in the cell stimulated by the HGF, phosphorylation of the Erk 1/2 was promoted in view of concentration dependence, and further phosphorylation of the Akt was also promoted.

Figure 12:
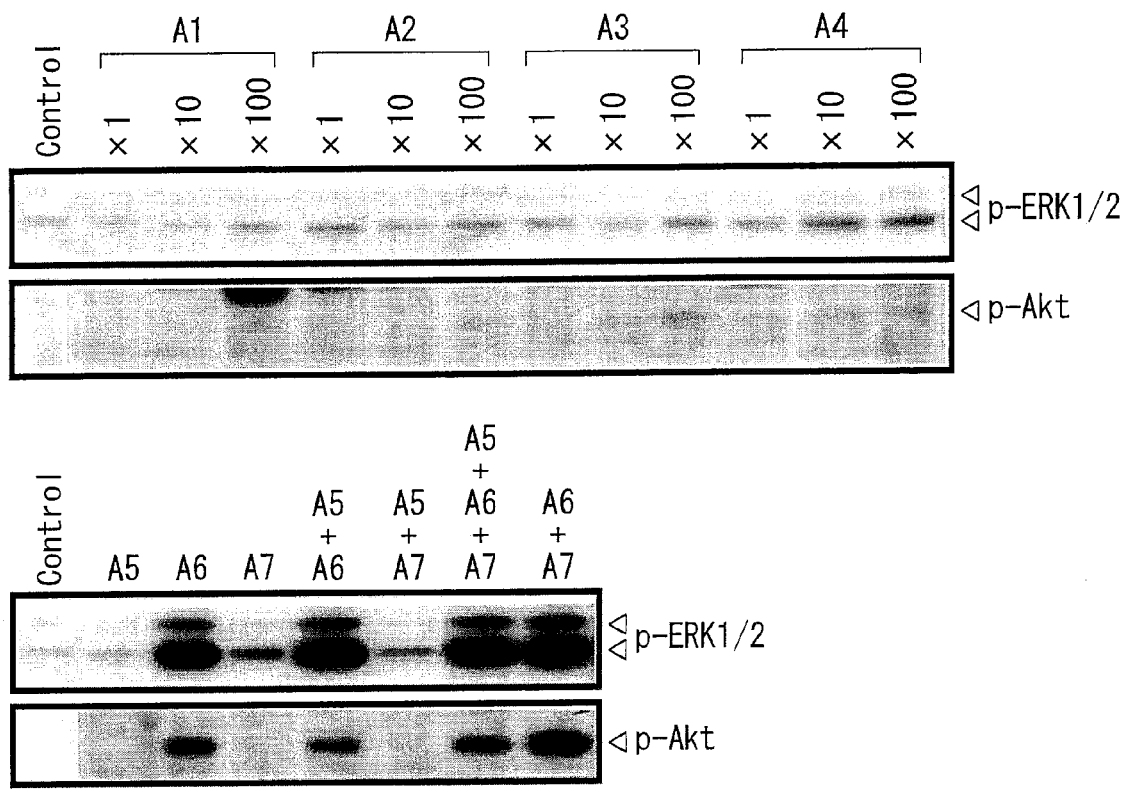
FIG. 12 illustrates how addition of a substance alternative to serum in serum-free culture media affected mitogenic signal transduction system of human mesenchymal stem cells (MSC).

FIG. 12 shows fractions of the proteins obtained from the cells stimulated by the fatty acid factors (A1 through A7). As shown in FIG. 12, compared with the controlled cell, phosphorylation of the Erk 1/2 and Akt was strongly promoted in the cell stimulated by the phosphatidic acid (A6). Further, phosphorylation of the Erk 1/2 was promoted in the cells stimulated by the arachidonic acid (A1), the linoleic acid (A2), the linolenic acid (A3), the oleic acid (A4) and the phosphatidyl choline (A7). That is to say, it was demonstrated that these fatty acid factors not only provided just energy and membrane components to the cultured cells, but also worked as growth factors and activated a mitogenic signal transduction system.

Example 8

Effects of Additional Base Factors in Serum-Free Culturing of Human Bone Marrow-Derived Mesenchymal Stem Cell It has been known that addition of lithium chloride (LiCl) to a culture medium containing 10% FBS activates a wingless/int (wnt) signal pathway, thereby promoting proliferation of a human mesenchymal stem cell. Further, L-glutathione acting as an antioxidant agent (a reducing agent) has been used for serum-free culturing of a human embryo-stem cell (ES cell). For the purpose of examining how lithium chloride (LiCl) and L-glutathione affect proliferation of a mesenchymal stem cell, human embryo-stem cells were cultured with the use of culture media, each of which was prepared by adding lithium chloride or L-glutathione to a serum-free culture medium described below.

Human iliac bone marrow fluid-derived mesenchymal stem cells were cultured in a $CO_2$ incubator with 5% $CO_2$ at 37° C. on a 10 cm plate including a DMEM culture medium containing 10% FBS, 100 unit/ml of penicillin, and 100 μg/ml of streptomycin. After becoming a subconfluent state, the cells were washed twice with PBS (−), and were then incubated for 2 minutes in PBS containing 0.05% trypsin and a 0.2 mM EDTA so that the cells were dispersed. The cells thus processed were re-suspended with a plant-derived trypsin inhibitor (Sigma T6522) that contains no serum. Further, after being washed three times with a DMEM culture medium containing no serum, the cultured cells were counted by use of a Coulter counter (Z1 Single, Coulter Co.). The thus re-suspended cells were re-inoculated on a 96-well plate at a density of 5000 cells/cm² with the use of the following different culture media.
(Culture medium 2) 10% FBS
(Culture medium 4-2) Growth factors, fatty acids and phospholipids (PA, PC)+EGF+VC
(Culture medium 4-4) Culture medium 4-2+lithium chloride (1 mM, Sigma L4408)
(Culture medium 4-5) Culture medium 4-2+L-glutathione (2 μg/ml, Sigma G6013)

The experiments were conducted with three samples per culture medium (n=3). The culture media were replaced every 2 or 3 days. On the eighth day in the culturing, the cells were counted by use of a cell counting kit WST-8 (Dojindo Lab.). The results are shown in FIGS. 15 (a) and (b).

Figure 15:
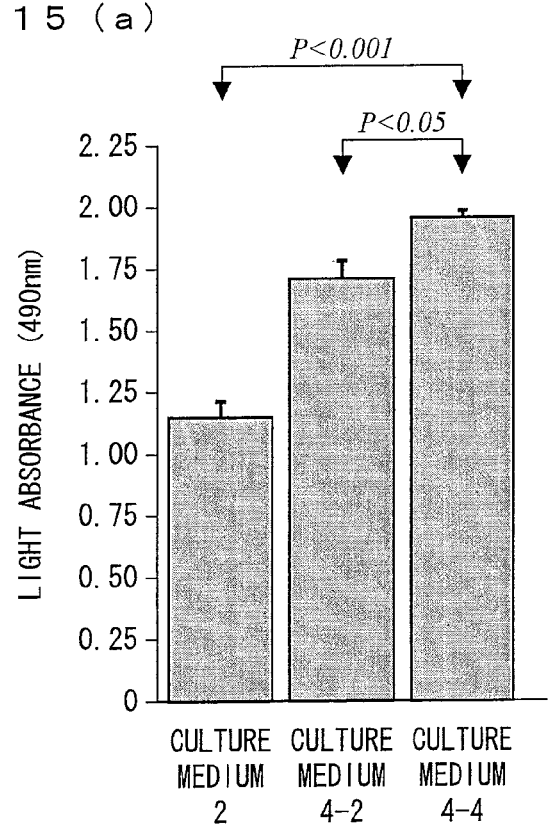
FIG. 15 (*a*) is a graph illustrating how addition of a substance alternative to serum in serum-free culture media affected proliferation of human mesenchymal stem cells (MSC).
Figure 15:
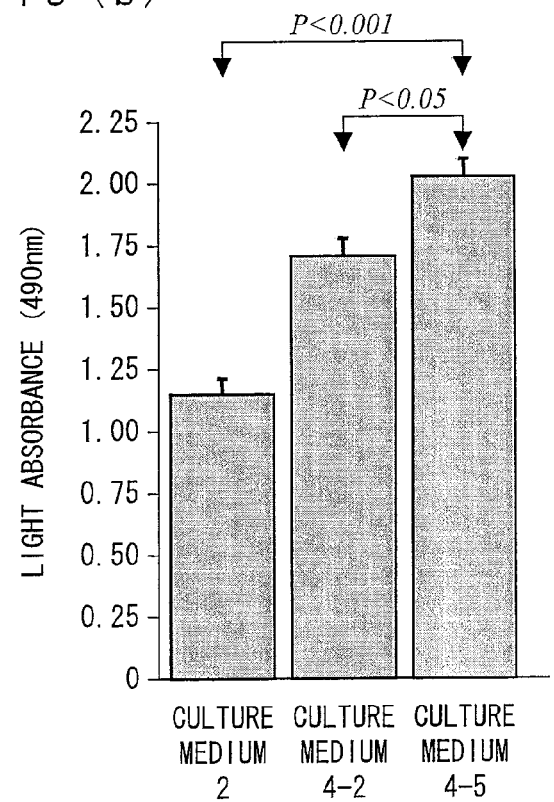

As shown in FIG. 15 (a), compared with proliferation potentials of the cells cultured in the culture media 4-2 and 2, a proliferation potential of the cells cultured in the culture medium 4-4 was remarkably high on the eighth day in the culture (numeric values indicate averages±SD, as a result of the experiments conducted with three samples per culture medium).

As shown in FIG. 15 (b), compared with the proliferation potentials of the cells cultured in the culture media 4-2 and 2, the proliferation potential of the cells cultured in the culture medium 4-5 was remarkably high on the eighth day in the culture (numeric values indicate averages±SD, as a result of the experiments conducted with three samples per culture medium).

Example 9

Effects of Growth Factors in Serum-Free Primary Culture Of Bone Marrow-Derived Mesenchymal Stem Cell For the purpose of studying growth factors to be added in a culture medium for culturing a primary cultured stem cell, ilium-derived bone marrow fluid was taken from a patient of Hiroshima University Hospital with the consent of the ethical committee of Hiroshima University Hospital and the patient. With the use of a density gradient centrifugation method, a mononuclear cell fraction (including MSCs) was separated from the ilium-derived bone marrow fluid. The mononuclear cell fraction was cultured in a $CO_2$ incubator with 5% $CO_2$ at 37° C. on a 24-well plate at a density of $1 \times 10^6$ (nuclear) cell/cm² with the use of the following culture media.

The culturing was carried out with the following culture media whose basal medium was DMEM/MCDB=1:1, and to which the following additives were added.
(Culture medium 1) No additives
(Culture medium 2) 10% FBS (fatal bovine serum)
(Culture medium 3) Growth factors and fatty acids
(Culture medium 4) Growth factors, fatty acids, and phospholipids (PA, PC)+EGF+VC (The culture medium 4-2 in FIG. 10)
(Culture medium 10-1) Only FGF was lacked from the culture medium 10.
(Culture medium 10-2) Only TGF-β was lacked from the culture medium 10
(Culture medium 10-3) Only HGF was lacked from the culture medium 10
(Culture medium 10-4) FGF and TGF-β were lacked from the culture medium 10
(Culture medium 10-5) FGF and HGF were lacked from the culture medium 10
(Culture medium 10-6) TGF-β and HGF were lacked from the culture medium 10
(Culture medium 10-7) FGF, TGF-β, and HGF were lacked from the culture medium 10
(Culture medium 11) MF-medium for mesenchymal stem cell proliferation (TMMFM-001, made by TOYOBO Co.)

The experiments were conducted with three samples (three cultivation systems) per culture medium (n=3). The culture media were replaced every 2 or 3 days. After the fourteenth day in the culture, the culture media were washed twice with PBS, and the cells were incubated in PBS containing 0.05% trypsin and 0.2 mM EDTA. Thus, the cells were collected. The collected cells were counted by use of a Coulter counter (Z1 Signal, Coulter Co.). The results are shown in FIGS. 16 (a) and (b).

As shown in FIG. 16 (a), it was demonstrated that the culture media 3 and 10, both of which have a high cell proliferation effect in subculturing, had a low promoting effect on cell proliferation in primary culture of a bone marrow-derived mesenchymal stem cell. This may be because a number of hematopoietic lineage cells in the bone marrow mononuclear cell fraction, except mesenchymal stem cells, affected proliferation of the mesenchymal stem cells. Since these nonadherent hematopoietic lineage cells are removed at every replacement of the culture media, the nonadherent hematopoietic lineage cells hardly exist after being subcultured once. On the other hand, when one through three growth factors were lacked from the culture media (i.e., the culture media 10-1 through 10-7), proliferation potentials of the mesenchymal stem cells cultured under a serum-free condition were improved. For example, in the culture medium 10-1, proliferation of the cultured cells was promoted. Further, in the culture medium 10-4, a proliferation potential of the cultured cells was obviously improved. Furthermore, a proliferation potential of the cultured cells remarkably increased in the culture medium 10-7 (numeric values indicate averages ±SD, as a result of the experiments conducted with three samples per culture medium). As such, it was demonstrated that it was required to change a composition of a substance alternative to serum in a case where a lot of cells except mesenchymal stem cells, such as hematopoietic cells, were present in a single serum-free culture medium.

Moreover, as shown in FIG. 16 (b), compared with the case where primary mesenchymal stem cells taken from bone marrow fluid were cultured in the culture medium 2 and the culture medium 11 that is commercially available, in a case where a primary mesenchymal cell taken from the bone marrow liquid was cultured in the culture medium 10-7, the cultured cell had further greater cell proliferation ($p<0.001$ in each of the experiments) (numeric values indicate averages±SD, as a result of the experiments conducted with three samples per culture medium).

Example 10

Serum-Free Culturing of Undifferentiated Cell Line

For the purpose of studying growth factors added into a culture medium for subculturing an undifferentiated cell, a mouse mesenchymal cell line 10T 1/2 (provided from RIKEN BioResource Center), a Chinese hamster ovary-derived cell line CHO cell (provided from RIKEN BioResource Center), and a human skin-derived fibroblast (provided from Health Science Research Resource Bank, HSRRB) were cultured in the following culture media.

The culturing was carried out with the following culture media whose basal culture medium was DMEM/MCDB=1:1, and to which the following additives were added.
(Culture medium 1) No additives
(Culture medium 2) 10% FBS (fatal bovine serum)
(Culture medium 10-5) FGF and HGF were lacked from the culture medium 10.
(Culture medium 10-7) FGF, TGF-β and HGF were lacked from the culture medium 10.
(Culture medium 10-8) FGF, TGF-β, HGF and PDGF were lacked from the culture medium 10.

10T 1/2 cells, CHO cells and fibroblasts were cultured in a $CO_2$ incubator with 5% $CO_2$ at 37° C. on a 10 cm plate including a DMEM culture containing 10% fatal bovine serum, 100 unit/ml of penicillin and 100 μg/ml of streptomycin. After becoming subconfluent, the cells were washed with PBS (−), and were then incubated for 2 minutes in PBS containing 0.05% trypsin and 0.2 mM EDTA. Thus, the cells were detached from the plate. The detached cells were re-suspended with a plant-derived trypsin incubator (Sigma T6522) that contains no serum. After being washed three times with a DMEM culture medium that contains no serum, the cells were counted by use of a Coulter counter (D1 Single, Coulter Co.). Further, the re-suspended cells were re-inoculated on a 96-well plate at a density of 5000 cells/$cm^2$ with the use of the above different culture media. The experiments were conducted with three samples per culture medium. The culture media were replaced every 2 or 3 days. On the eighth day in the culture, the cells were counted by use of a cell counting kit WST-8 (Dojindo Lab.). The results are shown in FIGS. 17 (a) through (c).

Figure 17A:
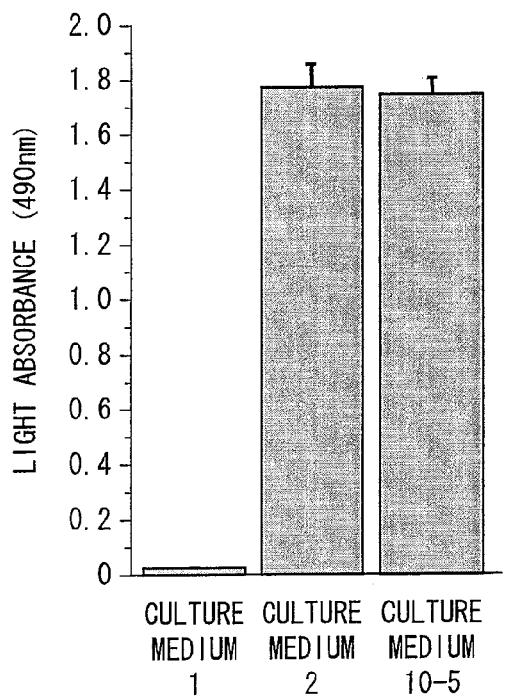
FIG. 17 (*a*) is a graph illustrating how addition of a substance alternative to serum in serum-free culture media affected proliferation of 10T 1/2 cells.
Figure 17C:
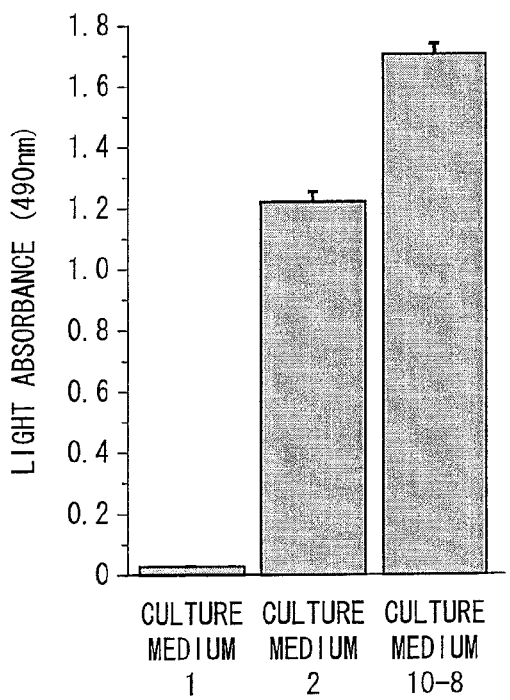
Figure 17B:
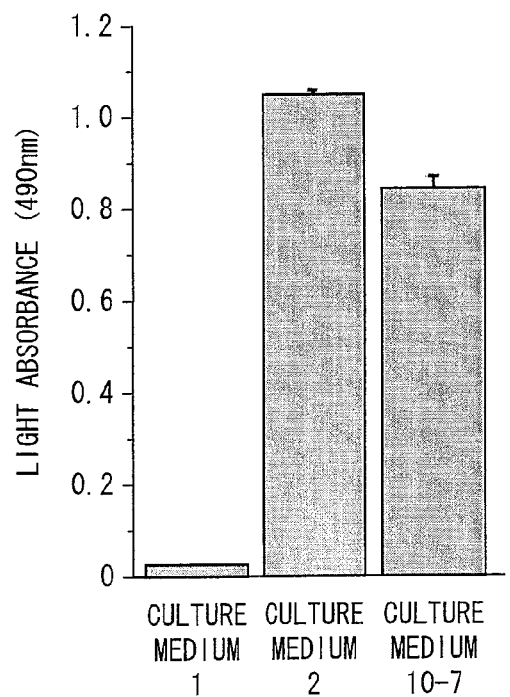

As shown in FIG. 17 (a), the cell line 10T 1/2 cells cultured in the culture medium 10-5 had a cell proliferation potential substantially equal to that of the cell line 10T 1/2 cells cultured in the culture medium 2 (numeric values indicate averages±SD, as a result of the experiments conducted with three samples per culture medium). Further, as shown in FIG. 17 (b), the CHO cells cultured in the culture medium 10-7 had an effective cell proliferation potential (numeric values indicate averages ±SD, as a result of the experiments that were conducted with three samples). Furthermore, as shown in FIG. 17 (c), compared with the fibroblasts cultured in the culture medium 2, the fibroblasts cultured in the culture medium 10-8 had a remarkably high cell proliferation potential on the eighth day in the culturing (numeric values indicate averages±SD, as a result of the experiments conducted with three samples).

According to the present invention, even in a serum-free culture medium, an animal cell can proliferated at a speed equal to or faster than culture in a culture medium containing 10% serum, and can be proliferated without losing its characteristics. Cell proliferation effects differ individually due to serum. However, according to the present invention, it is not necessary to consider the individual differences. Further, according to the present invention, it is possible to continuously subculture a human mesenchymal stem cell while maintaining at a high level its characteristics (such as an osteogenic differentiation potential and an adipogenic differentiation potential).

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The present invention makes it possible to have a decrease in cost by decreasing a necessary concentration of serum for cell culture, and to provide safely and at low cost a mesenchymal stem cell for use in regenerative medicine.

The invention claimed is:
1. A culture medium additive for use in serum-free culturing of a mesenchymal stem cell or a monkey kidney-derived undifferentiated cell line COS7 cell, the culture medium additive consisting of:
  (a) FGF, PDGF, TGF-β, and HGF;
  (b) two or more factors selected from the group consisting of EGF, CTGF, VEGF and ascorbic acid compound;
  (c) one or more phospholipids;
  (d) one or more fatty acids;
  (e) one of the following components (i) to (iv):
    (i) PLURONIC F-68 (polyoxyethylene-polyoxypropylene block copolymer) or TWEEN-80 (polyoxyethylene sorbitan monooleate),
    (ii) dexamethasone,
    (iii) PLURONIC F-68 (polyoxyethylene-polyoxypropylene block copolymer) and dexamethasone, or TWEEN-80 (polyoxyethylene sorbitan monooleate) and dexamethasone, and
    (iv) PLURONIC F-68 (polyoxyethylene-polyoxypropylene block copolymer) and dexamethasone, or TWEEN-80 (polyoxyethylene sorbitan monooleate);

(f) optionally, one or more of the following components (v) to (viii):
   (v) cholesterol,
   (vi) a lipid oxidation inhibitor,
   (vii) lithium chloride, and
   (viii) insulin, transferrin and selenate.

2. The culture medium additive as set forth in claim 1, wherein the phospholipid is selected from the group consisting of phosphatidic acid, lysophosphatidic acid, phosphatidylinositol, phosphatidylserine, phosphatidylethanolamine, phosphatidyl choline, and phosphatidylglycerol.

3. The culture medium additive as set forth in claim 1, wherein the fatty acid is selected from the group consisting of linoleic acid, oleic acid, linolenic acid, arachidonic acid, myristic acid, palmitoyl acid, palmitic acid, and stearic acid.

4. The culture medium additive as set forth in claim 3, wherein cholesterol is present.

5. The culture medium additive as set forth in claim 1, wherein a lipid oxidation inhibitor is present.

6. The culture medium additive as set forth in claim 5, wherein the lipid oxidation inhibitor is DL-α-tocopherol acetate (vitamin E), L-glutathione, or 2-mercaptoethanol.

7. The culture medium additive as set forth in claim 1, wherein lithium chloride is present.

8. The culture medium additive as set forth in claim 1, wherein insulin, transferrin, and selenate are present.

* * * * *